United States Patent
Spears et al.

(10) Patent No.: US 11,015,226 B2
(45) Date of Patent: May 25, 2021

(54) TARGETING THE HISTONE PATHWAY TO DETECT AND OVERCOME ANTHRACYCLIN RESISTANCE

(71) Applicant: ONTARIO INSTITUTE FOR CANCER RESEARCH (OICR), Toronto (CA)

(72) Inventors: Melanie Spears, Etobicoke (CA); John M. Bartlett, Toronto (CA); Marsela Braunstein, Waterloo (CA); Paul M. Krzyzanowski, Toronto (CA); Irina Kalatskaya, Toronto (CA); Lincoln Stein, Toronto (CA)

(73) Assignee: ONTARIO INSTITUTE FOR CANCER RESEARCH (OICR), Toronto (CA)

( * ) Notice: Subject to any disclaimer, the term of this patent is extended or adjusted under 35 U.S.C. 154(b) by 114 days.

(21) Appl. No.: 15/766,583

(22) PCT Filed: Oct. 4, 2016

(86) PCT No.: PCT/CA2016/000247
§ 371 (c)(1),
(2) Date: Apr. 6, 2018

(87) PCT Pub. No.: WO2017/059521
PCT Pub. Date: Apr. 13, 2017

(65) Prior Publication Data
US 2018/0282819 A1 Oct. 4, 2018

Related U.S. Application Data

(60) Provisional application No. 62/237,928, filed on Oct. 6, 2015.

(51) Int. Cl.
| | |
|---|---|
| *C12Q 1/6886* | (2018.01) |
| *A61K 31/704* | (2006.01) |
| *G01N 33/574* | (2006.01) |
| *G16B 25/00* | (2019.01) |
| *A61K 31/136* | (2006.01) |
| *A61K 45/06* | (2006.01) |

(52) U.S. Cl.
CPC .......... *C12Q 1/6886* (2013.01); *A61K 31/136* (2013.01); *A61K 31/704* (2013.01); *A61K 45/06* (2013.01); *G01N 33/57484* (2013.01); *G16B 25/00* (2019.02); *C12Q 2600/106* (2013.01); *C12Q 2600/158* (2013.01); *G01N 2800/52* (2013.01)

(58) Field of Classification Search
CPC .......... C12Q 1/6886; C12Q 2600/106
See application file for complete search history.

(56) References Cited

U.S. PATENT DOCUMENTS

2006/0160114 A1* 7/2006 Kerfoot ............... C12Q 1/6886
435/6.16

FOREIGN PATENT DOCUMENTS

| WO | WO 2007/085497 | * | 8/2007 |
| WO | WO 2014/047723 | | 4/2014 |

OTHER PUBLICATIONS

Braunstein et al. in Cancer Research 2013:73(24 Suppl): Abstract nr P5-08-14 (Year: 2013).*
Tate et al. in Breast Cancer Research 2012, 14; R79, 1-15 (Year: 2012).*
HIST2H2BE at https://en.wikipedia.org/wiki/HIST2H2BE (retrieved from the internet May 14, 2020) (Year: 2020).*
HIST2H2BD at https://en.wikipedia.org/wiki/HIST1H2BD (retrieved from the internet May 15, 2020) (Year: 2020).*
Villeneuve et al. in Breast Cancer Research and Treatment (2006) 96: 17-39 (Year: 2006).*
Braunstein et al. Deregulated histone H2A and H2B pathways are associated with anthracycline resistance in breast cancer. OICR Poster, 2013. (Year: 2013).*
Braunstein et al. Deregulated histone H2A and H2B pathways are associated with anthracycline resistance in breast cancer. OICR Poster, 2013.*
Bartlett et al., "Predicting Anthracycline Benefit: TOP2A and CEP17—Not Only but Also" *J. Clin Oncol.*, 2015, 33(15):1680-1687.
Beck et al., "Quantitative Proteomic Analysis of Post-translational Modifications of Human Histones" *Mol Cell Proteomics*, 2006, 5:1314-1325.
Bonenfant et al., "Characterization of Histone H2A and H2B Variants and Their Post-translational Modifications by Mass Spectrometry" *Mol Cell Proteomics*, 2006, 5:541-552.
Braunstein et al., "Abstract: P5-08-14: Deregulated histone and cell cycle pathways are associated with anthracycline resistance in breast cancer" *Cancer Research*, 2013, 73(24), accessed from the internet on Nov. 27, 2018; URL < http://cancerres.aacrjournals.org/content/73/24_Supplement/P5-08-14 >.
Braunstein et al., "Downregulation of Histone H2A and H2B pathways is associated with anthracycline sensitivity in breast cancer" *Breast Cancer Research*, 2016, 18, 16 pages.
Breitling et al., "Rank products: a simple, yet powerful, new method to detect differentially regulated genes in replicated microarray experiments" *FEBS Lett*, 2004, 573:83-92.
Chazard et al., "Taxol (paclitaxel), first molecule of a new class of cytotoxic agents: taxanes" *Bull Cancer*, 1994, 81:173-181.
Chernova et al., "Histone modifications and cancer: biomarkers of prognosis?" *American Journal of Cancer Research*, 2012, 2(5):589-597.
De Jong et al., "Reduced DNA Topoisomerase II Activity and Drug-Induced DNA Cleavage Activity in an Adriamycin-resistant Human Cell Lung Carcinoma Cell Line" *Cancer Res.*, 1990, 50:304-309.

(Continued)

*Primary Examiner* — Dennis Heyer
(74) *Attorney, Agent, or Firm* — Norton Rose Fulbright US LLP

(57) ABSTRACT

There is provided herein a method for determining a likelihood of resistance to anthracyclin, or poor survival, in a patient with cancer by identifying upregulation of at least one histone gene in the patient.

9 Claims, 28 Drawing Sheets

(56) References Cited

OTHER PUBLICATIONS

Early Breast Cancer Trialists' Collaborative Group (EBCTCG), "Effects of chemotherapy and hormonal therapy for early breast cancer on recurrence and 15-year survival: an overview of the randomised trials." *Lancet*, 2005, 365:1687-1717.
Friesen et al., "Deficient activation of the CD95 (APO-1/Fas) system in drug-resistant cells" *Leukemia*, 1997, 11:1833-1841.
Giaccone et al., "Multidrug Sensitivity Phenotype of Human Lung Cancer Cells Associated with Topoisomerase II Expression" *Cancer Res.*, 1992, 52:1666-1674.
Gosland et al., "Reversal of doxorubicin, etoposide, Vinblastine, and taxol resistance in multidrug resistant human sarcoma cells by polymer of spermine," *Cancer Chemother Pharmacol*, 1996, 37:593-600.
Groselj et al., "Histone deacetylase inhibitors as radiosensitisers: effects on DNA damage signaling and repair" *Br J Cancer*, 2013, 108:748-754.
Guo et al., "Cross-resistance studies of isogenic drug-resistant breast tumor cell lines support recent clinical evidence suggesting that sensitivity to paclitaxel may be strongly compromised by prior doxorubicin exposure." *Breast Cancer Res Treat*, 2004, 85:31-51.
Györffy et al., "An online survival analysis tool to rapidly assess the effect of 22,277 genes on breast cancer prognosis using microarray data of 1,809 patients" *Breast Cancer Res Treat*, 2010, 123:725-731.
Harris et al., "Regulation of histone mRNA in the unperturbed cell cycle: evidence suggesting control at two posttranscriptional steps." *Mol Cell Biol*, 1991, 11:2416-2424.
Hembruff et al., "Role of drug transporters and drug accumulation in the temporal acquisition of drug resistance" *BMC Cancer*, 2008, 8:318.
Illumina Inc., "Illumina HumanHT-12 V4.0 expression breadchip" NCBI Geo, 2010, Accession GPL 10558, Retrieved from the Internet on Nov. 27, 2018, URL <www.ncbi.nlm.nih.gov/geo/query/acc.cgi?acc=GPL10558 >.
International Search Report and Written Opinion issued in International Patent Application No. PCT/CA2016/000247, dated Dec. 21, 2016.
Kanehisa et al., "Data, information, knowledge and principle: back to metabolism in KEGG" *Nucleic Acids Res*, 2014, 42:D199-D205.
Lee et al., "Mechanisms of resistance to histone deacetylase inhibitors." *Adv Cancer Res*, 2012, 116:39-86.
Lowe et al., "p53-dependent apoptosis modulates the cytotoxicity of anticancer agents" *Cell*, 1993, 74: 957-967.
Minotti et al., "Anthracyclines: Molecular Advances and Pharmacologic Developments in Antitumor Activity and Cardiotoxicity" *Pharmacol Rev*, 2004, 56:185-229.
Munro et al., "Chromosome instability and benefit from adjuvant anthracyclines in breast cancer," *Br J Cancer*, 2012, 107:71-74.
Paridaens et al., "Paclitaxel Versus Doxorubicin as First-Line Single-Agent Chemotherapy for Metastatic Breast Cancer: A European Organization for Research and Treatment of Cancer Randomized Study With Cross-Over" *J Clin Oncol.*, 2000, 18:724-733.
Parra et al., "Deciphering the Roles of Histone H2B N-Terminal Domain in Genome-Wide Transcription" *Mol Cell Biol.*, 2006, 26:3842-3852.
Perou et al., "Molecular portraits of human breast tumours." *Nature*, 2000, 406:747-752.
Poole et al., "Epirubicin and Cyclophophamide, Methotrexate, and Fluorouracil as Adjuvant Therapy for Early Breast Cancer" 2006, 355:1851-1862.
Pritchard et al., "Chromosome 17 centromere (CEP17) duplication as a predictor of anthracycline response: evidence from the NCIC Clinical Trials Group (NCIC CTG) MA.5 Trial." *Breast Cancer Res Treat*, 2012, 131:541-551.
Regel et al., "Pan-Histone Deacetylase Inhibitor Panobinostat Sensitizes gastric Cancer Cells to Anthracyclines via Induction of CITED2" *Gastroenterology*, 2012, 143:99-109.
Ringel et al., "Studies with RP 56976 (Taxotere): a semisynthetic analogue of taxol" *J. Natl Cancer Inst*, 1991, 83:288-291.
Sanchez-Gonzalez et al., "Antileukemia activity of the combination of anthracycline with histone deacetylase inhibitor," *Blood*, 2006, 108(4):1174-1182.
Schinkel et al., "Characterization of the Human MDR3 P-Glycoprotein and Its Recognition by P-Glycoprotein-specific Monoclonal Antibodies" *Cancer Res*, 1991, 51:2628-2635.
Sorlie et al., "Gene expression patterns of breast carcinomas distinguish tumor subclasses with clinical implications" *Proc Natl Acad Sci U.S.A.*, 2001, 98:10869-10874.
Van der Bliek et al., "Genes Amplified and Overexpressed in Human Multidrug-resistant Cell Lines" *Cancer Res*, 1988, 48:5927-5932.
Wagner et al., "Histone deacetylase (HDAC) inhibitors in recent clinical trials for cancer therapy" *Clin Epigenetics*, 2010, 1:117-136.
Whitfield et al., "Stem-Loop Binding Protein, the Protein that Binds the 3' End of Histone mRNA, Is Cell Cycle Regulated by Both Translational and Posttranslational Mechanisms," *Mol Cell Biol.*, 2000, 20:4188-4198.
Wyrick et al., "The role of histone H2A and H2B post-translational modifications in transcription: a genomic perspective" *Biochim Biophys Acta*, 2009, 1789:37-44.
Münster et al., "Phase I Trial of Histone Deacetylase Inhibition by Valproic Acid Followed by the Topoisomerase II Inhibitor Epirubicin in Advanced Solid Tumors: A Clinical dn Translational Study" *Journal of Clinical Oncology*, 2007, 25(15):1979-1985.
Nayak et al., "A Role for Histone H2B Variants in Endocrine-Resistant Breast Cancer" *Hormones and Cancer*, 2015, 6(5):214-224.
Search Report issued in Corresponding European Patent Application No. 16852924, dated Apr. 10, 2019.
Villeneuve et al., "cDNA microarray analysis of isogenic paclitaxel and doxorubicin-resistant breast tumor cell lines reveals distinct drug-specific genetic signatures of resistance" *Breast Cancer Research and Treatment*, 2006, 96(1):17-39.

\* cited by examiner

IC₅₀ values (nM) and resistance factors

| | MCF7 | | MDA-MB-231 | | SKBR3 | | ZR-75-1 | |
|---|---|---|---|---|---|---|---|---|
| | Native | Resistant | Native | Resistant | Native | Resistant | Native | Resistant |
| Epirubicin | 15 ± 2.8 | 357 ± 37.8 (22) | 17 ± 4.4 | 634 ± 97.0 (67) | 30 ± 3.6 | 1937 ± 221.1 (46) | 47 ± 9.9 | 261 ± 8.2 (7) |
| Doxorubicin | 25 ± 6.1 | 377 ± 71.2 (15) | 23 ± 4.0 | 834 ± 42.2 (36) | 58 ± 7.1 | 1580 ± 119.1 (27) | 59.2 ± 13.4 | 335 ± 46.8 (6) |
| Paclitaxel | 1.8 ± 0.5 | 3.0 ± 0.7 (2) | 2.1 ± 0.4 | 2.7 ± 0.1 (1) | 2.8 ± 0.8 | 556 ± 79.3 (200) | 2.3 ± 0.7 | 2.9 ± 0.4 (1) |
| Docetaxel | 0.8 ± 0.1 | 1.2 ± 0.2 (2) | 0.8 ± 0.1 | 1.8 ± 0.5 (2) | 1.6 ± 0.1 | 293 ± 59.5 (180) | 0.9 ± 0 | 0.9 ± 0.3 (1) |
| SN-38 | 2.0 ± 0.3 | 10 ± 2.3 (5) | 4.5 ± 1.9 | 696 ± 115.2 (155) | 2.6 ± 0.8 | 46 ± 17.5 (18) | 4.0 ± 2 | 11 ± 5.5 (3) |
| Carboplatin* | 51 ± 18.9 | 105 ± 9.2 (2) | 50 ± 12.4 | 85 ± 27.6 (2) | 17 ± 4.8 | 9.1 ± 1.1 (0.5) | 156 ± 29.8 | 262 ± 24.5 (2) |

Resistance factor (bold numbers in brackets) represents resistant IC₅₀/native IC₅₀.
* Denotes that IC₅₀ values for this drug are in μM.

Figure 1B

| Pathways | FDR | Contributing Genes |
|---|---|---|
| Chromosome Maintenance(R) | <1.00e-03 | HIST1H2AC,HIST1H2BD,HIST1H2BK,NHP2 |
| Amyloids(R) | <5.00e-04 | HIST1H2AC,HIST1H2BD,HIST1H2BK |
| Mitotic M-M/G1 phases(R) | <3.33e-04 | HIST1H2AC,HIST1H2BD,HIST1H2BK,ARPP19 |
| Meiosis(R) | 2.50E-04 | HIST1H2AC,HIST1H2BD,HIST1H2BK |
| Epigenetic pathways(R) | 4.00E-04 | HIST1H2AC,HIST1H2BD,HIST1H2BK |
| RNA Polymerase I/III and Mitochondrial Transcription(R) | 3.33E-04 | HIST1H2AC,HIST1H2BD,HIST1H2BK |
| Post-translational protein modification(R) | 5.22E-03 | HIST1H2AC,HIST1H2BD,HIST1H2BK |

Figure 4E

Multivariate Cox proportional hazards regression model, treatment by marker analysis after adjustment for age, tumour size, nodal status, ER status, pathological grade and HER2 status

| | DRFS | | | OS | | |
|---|---|---|---|---|---|---|
| | HR | 95% CI | p-value | HR | 95% CI | p-value |
| Age | 0.98 | 0.59-1.61 | 0.928 | 1.18 | 0.72-1.94 | 0.504 |
| Tumour size | 1.05 | 0.60-1.86 | 0.859 | 1.19 | 0.65-2.15 | 0.577 |
| Nodal status | 3.42 | 1.27-9.27 | 0.015 | 2.69 | 1.06-6.79 | 0.037 |
| ER status | 1.39 | 0.80-2.41 | 0.248 | 1.72 | 0.99-3.01 | 0.056 |
| Pathological grade | 1.43 | 0.42-4.89 | 0.568 | 1.38 | 0.40-4.73 | 0.609 |
| HER2 status | 1.24 | 0.69-2.22 | 0.468 | 1.29 | 0.73-2.28 | 0.376 |
| Histone module | 0.35 | 0.13-0.96 | 0.042 | 0.50 | 0.19-1.31 | 0.159 |

HR, hazard ratio; 95% CI, 95% confidence interval;
DRFS, distant recurrence free survival; OS, overall survival

Figure 6B

TARGETING THE HISTONE PATHWAY TO DETECT AND OVERCOME ANTHRACYCLIN RESISTANCE

CROSS-REFERENCE TO RELATED APPLICATIONS

This application is a national phase application under 35 U.S.C. § 371 of International Application No. PCT/CA2016/000247 filed 4 Oct. 2016, which claims priority to U.S. Provisional Application No. 62/237,928 filed 6 Oct. 2015. The entire contents of each of the above-referenced disclosures is specifically incorporated by reference herein without disclaimer.

FIELD OF THE INVENTION

The invention relates to the targeting of the histone pathway in order to assess and overcome anthracycline resistance.

BACKGROUND OF THE INVENTION

Breast cancer is the second leading cause of cancer death for women. Most patients present with early disease and are treated with surgery often followed by adjuvant radiotherapy and chemotherapy+/–endocrine therapy or trastuzumab given with curative intent; nevertheless, 40-50% of high-risk patients treated with adjuvant chemotherapy ultimately relapse as a result of them having resistant disease (EBCTCG 2005). Despite the advent of targeted therapies, chemotherapy is also central to the treatment of women with metastatic disease, who often respond to palliative chemotherapy but in due course relapse due to drug resistance, including cross-resistance to structurally unrelated anti-cancer drugs (Guo et al. 2004).

The taxanes and anthracyclines are widely used as adjuvant therapy, but also in the metastatic setting. Both target rapidly proliferating cancer cells. The taxanes interfere with microtubule depolymerisation, causing cell-cycle arrest (Ringel and Horwitz 1991; Chazard et al. 1994), whereas anthracyclines introduce DNA breaks, form free radicals and covalently bind topoisomerase II-DNA complexes (Minotti et al. 2004; Minotti et al. 2004). The taxanes and anthracyclines are both natural products and susceptible to resistance mediated by over-expression of the multidrug transporter P-glycoprotein. A well-established in vitro mechanism of resistance involves activity of MDR1 and MDR2/3, which bind non-specifically to multiple drugs and actively export them across the cellular membrane (Schinkel et al. 1991; van der Bliek et al. 1988). Although this results in decreased intracellular drug concentrations and cytotoxicity, the clinical relevance of MDR genes remains to be determined. Other mechanisms include reduced topoisomerase activity (Giaccone et al. 1992; de Jong et al. 1990), reduced Fas ligand expression (Friesen et al. 1997) and downregulation of TP53 expression (Lowe et al. 1993). However, the molecular drivers of clinical anthracycline resistance remain largely unknown. Applicant previously identified duplication of centromeric region on chromosome 17 (CEP17), a surrogate marker of chromosomal instability, as a predictive marker of clinical anthracycline sensitivity (Munro et al. 2012; Pritchard et al. 2012; Bartlett et al. 2015). However, identifying pathways that could be targeted in the clinic to eliminate anthracycline-resistant breast cancer remains a major challenge.

SUMMARY OF THE INVENTION

In an aspect, there is provided a method for determining a likelihood of resistance to anthracycline in a patient with cancer comprising: providing a sample from the subject; detecting a level of expression in the sample of at least one gene in the regulatory pathway of at least one histone gene from the H1, H2A, H2B, H3 and H4 gene families; comparing the level of the at least one gene detected to a level of expression of the at least one gene in a control sample; and wherein there is a likelihood of anthracycline resistance if there is a relatively higher level of expression of the at least one gene in the subject sample compared to the control sample.

In an aspect, there is provided a method for prognosticating survival in cancer patient comprising: providing a sample from the subject; detecting a level of expression in the sample of at least one gene in the regulatory pathway of at least one histone gene from the H1, H2A, H2B, H3 and H4 gene families; comparing the level of the at least one gene detected to a level of expression of the at least one gene in a control sample; and wherein there is a likelihood of poor survival if there is a relatively higher level of expression of the at least one gene in the subject sample compared to the control sample.

In an aspect, there is provided a use of a histone deacetylase inhibitor in the treatment of a cancer patient receiving anthracycline and exhibiting upregulation of at least one histone gene.

In an aspect, there is provided a use of a histone deacetylase inhibitor in the treatment of a breast cancer patient receiving anthracycline.

In an aspect, there is provided a method of sensitizing, or re-sensitizing, a patient with breast cancer to anthracycline, comprising administering to the patient a histone deacetylase inhibitor.

In an aspect, there is provided a composition comprising a plurality of reagents, preferably nucleic acid sequences, wherein each of the reagents is for detecting a level of expression in the sample of a gene in the regulatory pathway of at least one histone gene from the H1, H2A, H2B, H3 and H4 gene families.

In an aspect, there is provided an array comprising, for a plurality of genes in the regulatory pathway of at least one histone gene from the H1, H2A, H2B, H3 and H4 gene families, one or more polynucleotide probes complementary and hybridizable to an expression product of the gene.

In an aspect, there is provided a kit for determining a likelihood of resistance to anthracycline in a patient, comprising detection agents for detecting a level of expression in the sample of a gene in the regulatory pathway of at least one histone gene from the H1, H2A, H2B, H3 and H4 gene families, and instructions for use.

In an aspect, there is provided a kit for prognosticating survival in cancer patient, comprising detection agents for detecting a level of expression in the sample of a gene in the regulatory pathway of at least one histone gene from the H1, H2A, H2B, H3 and H4 gene families, and instructions for use.

In an aspect, there is provided a computer program product for use in conjunction with a computer having a processor and a memory connected to the processor, the computer program product comprising a computer readable storage medium having a computer mechanism encoded thereon, wherein the computer program mechanism may be loaded into the memory of the computer and cause the computer to carry out the method of any one of claims 1-6.

In an aspect, there is provided a computer implemented product for determining a likelihood of resistance to anthracycline in a patient comprising: a means for receiving values corresponding to a subject expression profile in a subject sample; a database comprising a control expression profile associated with at least one gene in the regulatory pathway of at least one histone gene from the H1, H2A, H2B, H3 and H4 gene families; and processor disposed to compare the subject expression profile to the control expression profile and determine a likelihood of anthracycline resistance if there is a relatively higher level of expression of the at least one gene in the subject sample compared to the control sample.

In an aspect, there is provided a computer implemented product for prognosticating survival in cancer patient comprising: a means for receiving values corresponding to a subject expression profile in a subject sample; and a database comprising a control expression profile associated with at least one gene in the regulatory pathway of at least one histone gene from the H1, H2A, H2B, H3 and H4 gene families; and a processor disposed to compare the subject expression profile to the control expression profile and determine there is a likelihood of poor survival if there is a relatively higher level of expression of the at least one gene in the subject sample compared to the control sample.

BRIEF DESCRIPTION OF FIGURES

These and other features of the preferred embodiments of the invention will become more apparent in the following detailed description in which reference is made to the appended drawings wherein.

DETAILED DESCRIPTION

Figure 1A:
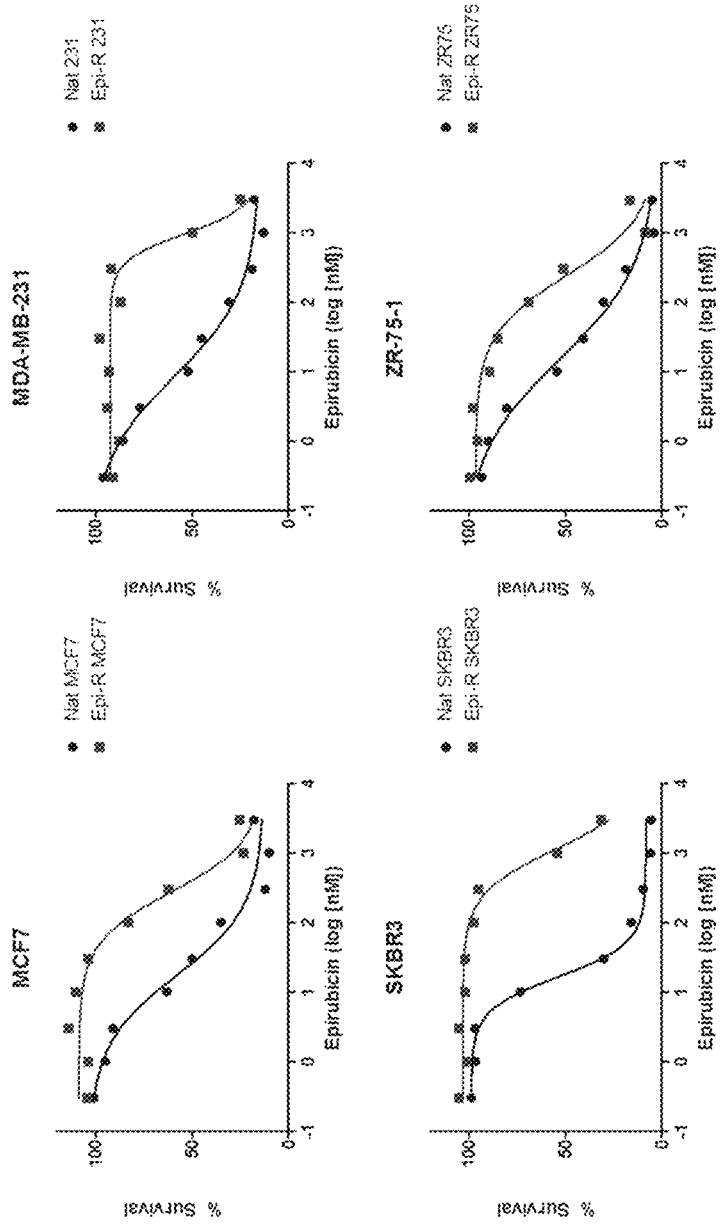
FIG. 1 shows characterization of epirubicin-resistant cell lines. Native and resistant cells were exposed to drug concentrations ranging from 0.3 nM to 3000 nM. Cell viability was determined 72h later by CCK-8 assay. A) Percent of live cells relative to DMSO control was plotted against epirubicin concentration. Black=native cells, magenta=resistant cells. B) $IC_{50}$ values in nM concentration±standard deviation. Resistance factor is shown in parenthesis and represents resistant $IC_{50}$/native $IC_{50}$.

In the following description, numerous specific details are set forth to provide a thorough understanding of the invention. However, it is understood that the invention may be practiced without these specific details.

Drug resistance in breast cancer is the major obstacle to effective treatment with chemotherapy. While upregulation of multidrug resistance (MDR) genes is a key component of drug resistance in multiple cancers, the complexity and hierarchy of non-MDR driven drug resistance pathways are still largely unknown. The present study aimed to establish anthracycline-resistant breast cancer cell lines to elucidate mechanisms driving resistance, which could be tested in clinical trial cohorts. Cell lines were chosen to reflect four major breast cancer subtypes (Perou et al. 2000; Sorlie et al. 2001): MCF7 (ER+HER2−, luminal A), ZR-75-1 (ER+ HER2+, luminal B), SKBR3 (ER−HER2+, HER2-amplified) and MDA-MB-231 (ER−/PR−/HER2−, triple negative), and exposed to increasing concentrations of epirubicin until resistant cells were generated. To identify mechanisms driving epirubicin resistance, the investigators used complementary approaches including gene expression analyses to identify signaling pathways involved in resistance, and small-molecule inhibitors to reverse resistance. Applicant demonstrated that overexpression of histones H2A and H2B were associated with epirubicin resistance and that small-molecule inhibitors targeting histone pathways reversed resistance and induced cytotoxicity in all epirubicin-resistant cell lines. Most importantly, the identified mechanism of resistance was recapitulated in the BR9601 clinical trial as the patients with low expression of the histone module benefited from anthracycline treatment compared to patients with high expression of the same module (HR: 0.35, 95% CI 0.13-0.96, p=0.042). Thus, our study has identified that chromatin remodeling represents an important mechanism of anthracycline resistance in breast cancer and established a reliable in vitro model system for investigating anthracycline resistance in all four breast cancer subtypes; as the histone modification can be targeted with small-molecule inhibitors, it presents a possible means of reversing clinical anthracycline resistance.

In an aspect, there is provided a method for determining a likelihood of resistance to anthracycline in a patient with cancer comprising: providing a sample from the subject; detecting a level of expression in the sample of at least one gene in the regulatory pathway of at least one histone gene from the H1, H2A, H2B, H3 and H4 gene families; comparing the level of the at least one gene detected to a level of expression of the at least one gene in a control sample; and wherein there is a likelihood of anthracycline resistance if there is a relatively higher level of expression of the at least one gene in the subject sample compared to the control sample.

In an aspect, there is provided a method for prognosticating survival in cancer patient comprising: providing a sample from the subject; detecting a level of expression in the sample of at least one gene in the regulatory pathway of at least one histone gene from the H1, H2A, H2B, H3 and H4 gene families; comparing the level of the at least one gene detected to a level of expression of the at least one gene in a control sample; and wherein there is a likelihood of poor survival if there is a relatively higher level of expression of the at least one gene in the subject sample compared to the control sample.

Five major families of histones exist: H1/H5, H2A, H2B, H3 and H4.[2][4][5] Histones H2A, H2B, H3 and H4 are known as the core histones, while histones H1 and H5 are known as the linker histones.

The H1 family comprises the H1F subfamily comprising H1F0, H1FNT, H1FOO, and H1FX; and the H1H1 subfamily comprising HIST1H1A, IST1H1B, HIST1H1C, HIST1H1D, HIST1H1E and HIST1H1T.

The H2A family comprises the H2AF subfamily comprising H2AFB1, H2AFB2, H2AFB3, H2AFJ, H2AFV, H2AFX, H2AFY, H2AFY2 and H2AFZ; the H2A1 subfamily comprising HIST1H2AA, HIST1H2AB, HIST1H2AC, HIST1H2AD, HIST1H2AE, HIST1H2AG, HIST1H2A1, HIST1H2AJ, HIST1H2AK, HIST1H2AL, and HIST1H2AM; the H2A2 subfamily comprising HIST2H2AA3, HIST2H2AC.

The H2B family comprises the H2BF subfamily comprising H2BFM, H2BFS, and H2BFWT; the H2B1 subfamily comprising HIST1H2BA, HIST1 H2BB, HIST1 H2BC, HIST1 H2BD, HIST1H2BE, HIST1H2BF, HIST1H2BG, HIST1 H2BH, HIST1H2BI, HIST1H2BJ, HIST1H2BK, HIST1 H2BL, HIST1H2BM, HIST1 H2BN, and HIST1 H2BO; and the H2B2 subfamily comprising HIST2H2BE.

The H3 family comprises the H3A1 subfamily comprising HIST1H3A, HIST1H3B, HIST1H3C, HIST1H3D, HIST1H3E, HIST1H3F, HIST1H3G, HIST1H3H, HIST1H31, and HIST1H3J; the H3A2 subfamily comprising HIST2H3C; and the H3A3 subfamily comprising HIST3H3.

The H4 family comprises the H41 subfamily comprising HIST1H4A, HIST1 H4B, HIST1H4C, HIST1H4D, HIST1H4E, HIST1H4F, HIST1H4G, HIST1H4H, HIST1H41, HIST1H4J, HIST1H4K, and HIST1H4L; and the H44 subfamily comprising HIST4H4.

The aspects described herein may be practiced with any number of cancers. In some embodiments, the cancer is a multidrug resistant cancer. Cancers could include Adrenal Cancer, Anal Cancer, Bile Duct Cancer, Bladder Cancer, Bone Cancer, Brain/CNS Tumors, Breast Cancer, Castleman Disease, Cervical Cancer, Colon/Rectum Cancer, Endometrial Cancer, Esophagus Cancer, Ewing Family Of Tumors, Eye Cancer, Gallbladder Cancer, Gastrointestinal Carcinoid Tumors, Gastrointestinal Stromal Tumor (GIST), Gestational Trophoblastic Disease, Hodgkin Disease, Kaposi Sarcoma, Kidney Cancer, Laryngeal and Hypopharyngeal Cancer, Leukemia, Liver Cancer, Lung Cancer, Lung Carcinoid Tumor, Lymphoma, Malignant Mesothelioma, Multiple Myeloma, Myelodysplastic Syndrome, Nasal Cavity and Paranasal Sinus Cancer, Nasopharyngeal Cancer, Neuroblastoma, Non-Hodgkin Lymphoma, Oral Cavity and Oropharyngeal Cancer, Osteosarcoma, Ovarian Cancer, Pancreatic Cancer, Penile Cancer, Pituitary Tumors, Prostate Cancer, Retinoblastoma, Rhabdomyosarcoma, Salivary Gland Cancer, Sarcoma, Skin Cancer, Small Intestine Cancer, Stomach Cancer, Testicular Cancer, Thymus Cancer, Thyroid Cancer, Uterine Sarcoma, Vaginal Cancer, Vulvar Cancer, Waldenstrom Macroglobulinemia, and Wilms Tumor.

The term "level of expression" or "expression level" as used herein refers to a measurable level of expression of the products of biomarkers, such as, without limitation, the level of messenger RNA transcript expressed or of a specific exon or other portion of a transcript, the level of proteins or portions thereof expressed of the biomarkers, the number or presence of DNA polymorphisms of the biomarkers, the enzymatic or other activities of the biomarkers, and the level of specific metabolites.

In addition, a person skilled in the art will appreciate that a number of methods can be used to determine the amount of a protein product of the biomarker of the invention, including immunoassays such as Western blots, ELISA, and immunoprecipitation followed by SDS-PAGE and immunocytochemistry.

As used herein, the term "control" refers to a specific value or dataset that can be used to prognose or classify the value e.g. expression level or reference expression profile obtained from the test sample associated with an outcome class. A person skilled in the art will appreciate that the comparison between the expression of the biomarkers in the test sample and the expression of the biomarkers in the control will depend on the control used.

The term "differentially expressed" or "differential expression" as used herein refers to a difference in the level of expression of the biomarkers that can be assayed by measuring the level of expression of the products of the biomarkers, such as the difference in level of messenger RNA transcript or a portion thereof expressed or of proteins expressed of the biomarkers. In a preferred embodiment, the difference is statistically significant. The term "difference in the level of expression" refers to an increase or decrease in the measurable expression level of a given biomarker, for example as measured by the amount of messenger RNA transcript and/or the amount of protein in a sample as compared with the measurable expression level of a given biomarker in a control.

The term "sample" as used herein refers to any fluid, cell or tissue sample from a subject that can be assayed for biomarker expression products and/or a reference expression profile, e.g. genes differentially expressed in subjects.

In some embodiments, the at least one histone gene is from the H2A or H2B families, preferably selected from the group consisting of H2AFB1, H2AFB2, H2AFB3, H2AFJ, H2AFV, H2AFX, H2AFY, H2AFY2, H2AFZ, HIST1H2AA, HIST1H2AB, HIST1H2AC, HIST1H2AD, HIST1H2AE, HIST1H2AG, HIST1H2A1, HIST1H2AJ, HIST1H2AK, HIST1H2AL, HIST1H2AM, HIST2H2AA3, HIST2H2AC, H2BFM, H2BFS, H2BFWT, HIST1H2BA, HIST1H2BB, HIST1H2BC, HIST1H2BD, HIST1H2BE, HIST1H2BF, HIST1H2BG, HIST1H2BH, HIST1H2BI, HIST1H2BJ, HIST1H2BK, HIST1H2BL, HIST1H2BM, HIST1H2BN, HIST1H2B0, and HIST2H2BE; or any combinations thereof.

In some embodiments, the at least one histone gene is HIST1H2AC, HIST1H2BK, HIST1H2BD, or any combinations thereof.

In some embodiments, the at least one histone gene comprises any of the genes in Table 7 or combinations thereof. In an embodiment, the at least one histone gene comprises all of the genes in Table 7.

In some embodiments, the method further comprises treating the patient with adjuvant therapy that does not comprise anthracycline if there is a relatively higher level of expression of the at least one gene in the subject sample compared to the control sample.

In some embodiments, the method further comprises administering to the patient anthracycline along with an inhibitor of at least one gene in the regulatory pathway of at least one histone gene, if there is a relatively higher level of expression of the at least one gene in the subject sample compared to the control sample.

In some embodiments, the inhibitor is a histone deacetylase inhibitor, preferably panobinostat, quisinostat, givinostat, abexinostat, pracinostat, belinostat mocetinostat, Apicidin A, CAY10603, Oxamflatin, Trichostatin A, Sciptaid, CBHA or Dacinostat.

In some embodiments, the cancer is breast cancer, leukemias, lymphomas, breast, uterine, ovarian, bladder cancer, or lung cancers. In an embodiment, the breast cancer is early breast cancer, preferably selected from the following subtype: ER+HER2−, luminal A, ER+HER2+, luminal B, ER−HER2+, HER2−amplified and ER−/PR−/HER2−, triple negative.

In some embodiments, the anthracycline is Daunorubicin Doxorubicin, Epirubicin, Idarubicin, Valrubicin, or Mitoxantrone, preferably Epirubicin.

In an aspect, there is provided a use of a histone deacetylase inhibitor in the treatment of a cancer patient receiving anthracycline and exhibiting upregulation of at least one histone gene.

In an aspect, there is provided a use of a histone deacetylase inhibitor in the treatment of a breast cancer patient receiving anthracycline.

In an aspect, there is provided a method of sensitizing, or re-sensitizing, a patient with breast cancer to anthracycline, comprising administering to the patient a histone deacetylase inhibitor.

In an aspect, there is provided a composition comprising a plurality of reagents, preferably nucleic acid sequences, wherein each of the reagents is for detecting a level of expression in the sample of a gene in the regulatory pathway of at least one histone gene from the H1, H2A, H2B, H3 and H4 gene families.

In an aspect, there is provided an array comprising, for a plurality of genes in the regulatory pathway of at least one histone gene from the H1, H2A, H2B, H3 and H4 gene families, one or more polynucleotide probes complementary and hybridizable to an expression product of the gene.

In an aspect, there is provided a kit for determining a likelihood of resistance to anthracycline in a patient, comprising detection agents for detecting a level of expression in the sample of a gene in the regulatory pathway of at least one histone gene from the H1, H2A, H2B, H3 and H4 gene families, and instructions for use.

In an aspect, there is provided a kit for prognosticating survival in cancer patient, comprising detection agents for detecting a level of expression in the sample of a gene in the regulatory pathway of at least one histone gene from the H1, H2A, H2B, H3 and H4 gene families, and instructions for use.

In an aspect, there is provided a computer program product for use in conjunction with a computer having a processor and a memory connected to the processor, the computer program product comprising a computer readable storage medium having a computer mechanism encoded thereon, wherein the computer program mechanism may be loaded into the memory of the computer and cause the computer to carry out the method of any one of claims 1-6.

In an aspect, there is provided a computer implemented product for determining a likelihood of resistance to anthracycline in a patient comprising: a means for receiving values corresponding to a subject expression profile in a subject sample; a database comprising a control expression profile associated with at least one gene in the regulatory pathway of at least one histone gene from the H1, H2A, H2B, H3 and H4 gene families; and processor disposed to compare the subject expression profile to the control expression profile and determine a likelihood of anthracycline resistance if there is a relatively higher level of expression of the at least one gene in the subject sample compared to the control sample.

In an aspect, there is provided a computer implemented product for prognosticating survival in cancer patient comprising: a means for receiving values corresponding to a subject expression profile in a subject sample; and a database comprising a control expression profile associated with at least one gene in the regulatory pathway of at least one histone gene from the H1, H2A, H2B, H3 and H4 gene families; and a processor disposed to compare the subject expression profile to the control expression profile and determine there is a likelihood of poor survival if there is a relatively higher level of expression of the at least one gene in the subject sample compared to the control sample.

As used herein, "pharmaceutically acceptable carrier" means any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the pharmacological agent.

As used herein, "therapeutically effective amount" refers to an amount effective, at dosages and for a particular period of time necessary, to achieve the desired therapeutic result. A therapeutically effective amount of the pharmacological agent may vary according to factors such as the disease state, age, sex, and weight of the individual, and the ability of the pharmacological agent to elicit a desired response in the individual. A therapeutically effective amount is also one in which any toxic or detrimental effects of the pharmacological agent are outweighed by the therapeutically beneficial effects.

The advantages of the present invention are further illustrated by the following examples. The examples and their particular details set forth herein are presented for illustration only and should not be construed as a limitation on the claims of the present invention.

EXAMPLES

Methods and Materials
BR9601 Trial

Figure 8:
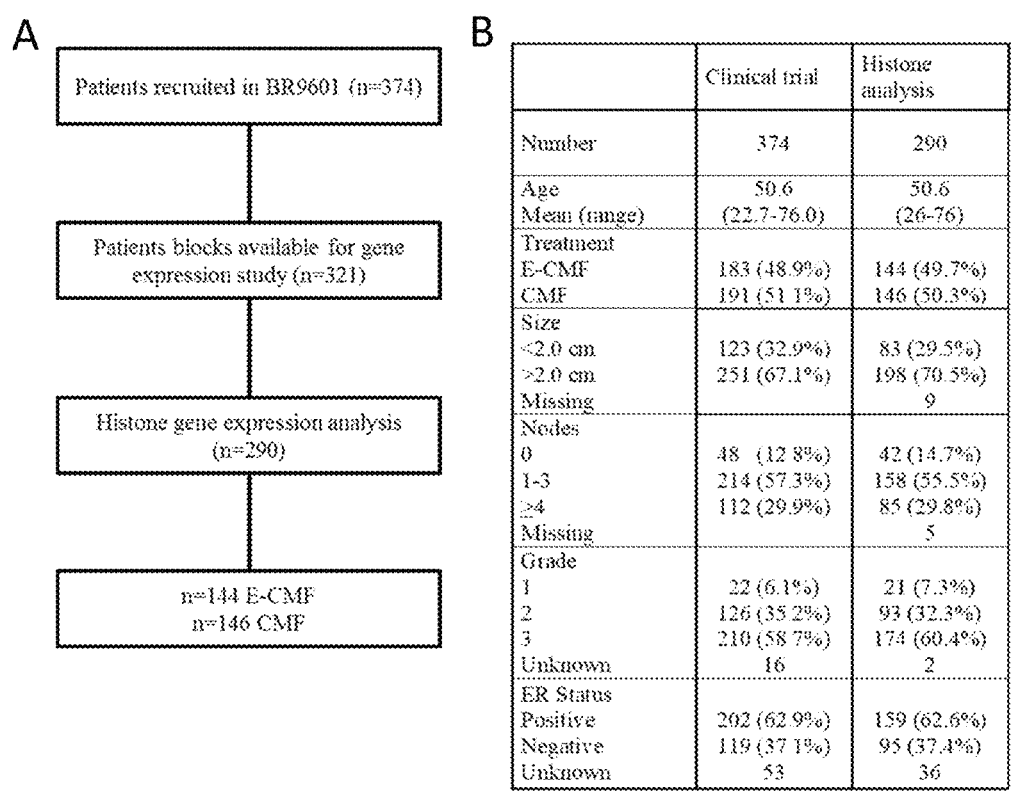
FIG. 8 shows clinical trial BR9601 information. A) Schematic representation of the patient samples available for analysis. B) Patient information available for the histone analysis.
Figure 9A:
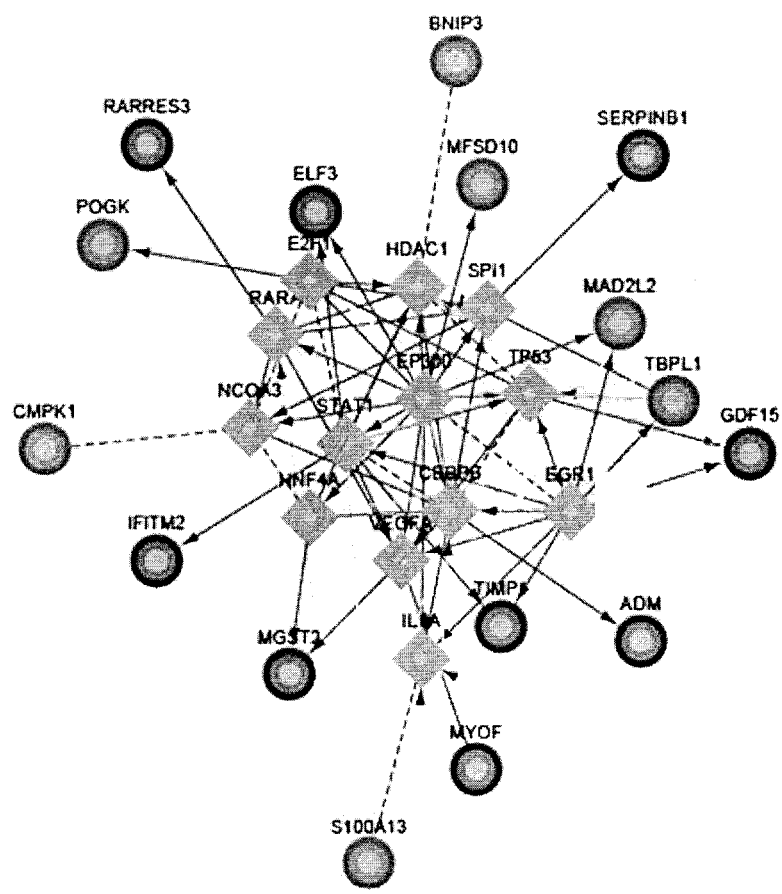
Figure 9B:
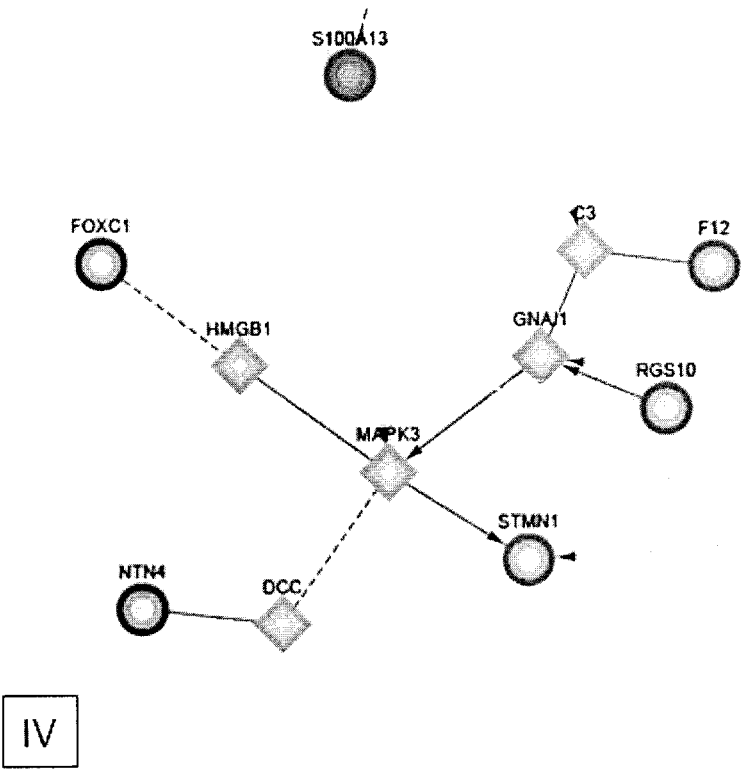
Figure 9C:
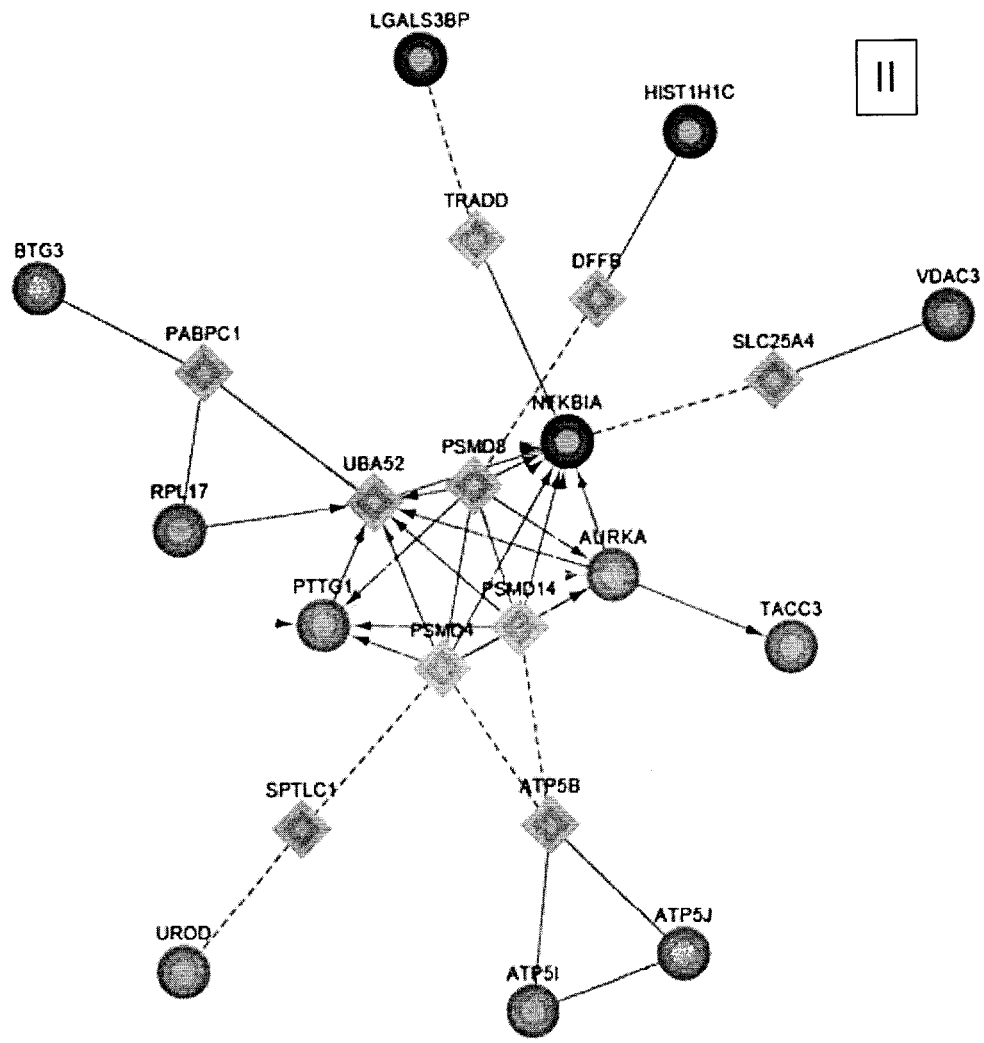
Figure 9D:
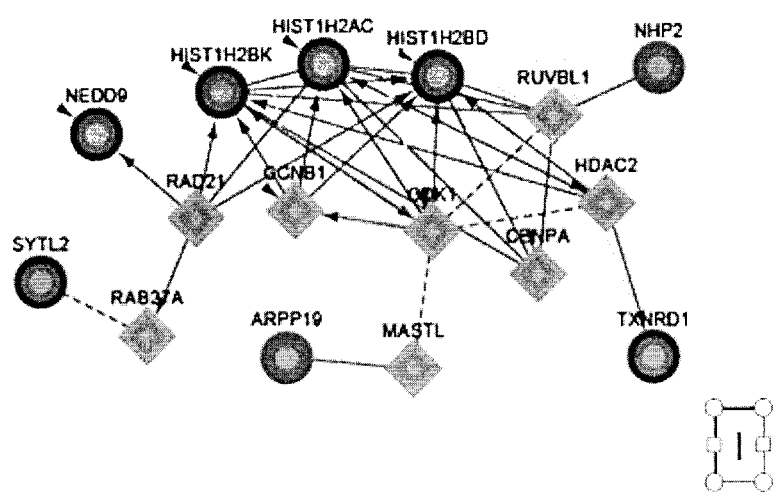
Figure 10A:
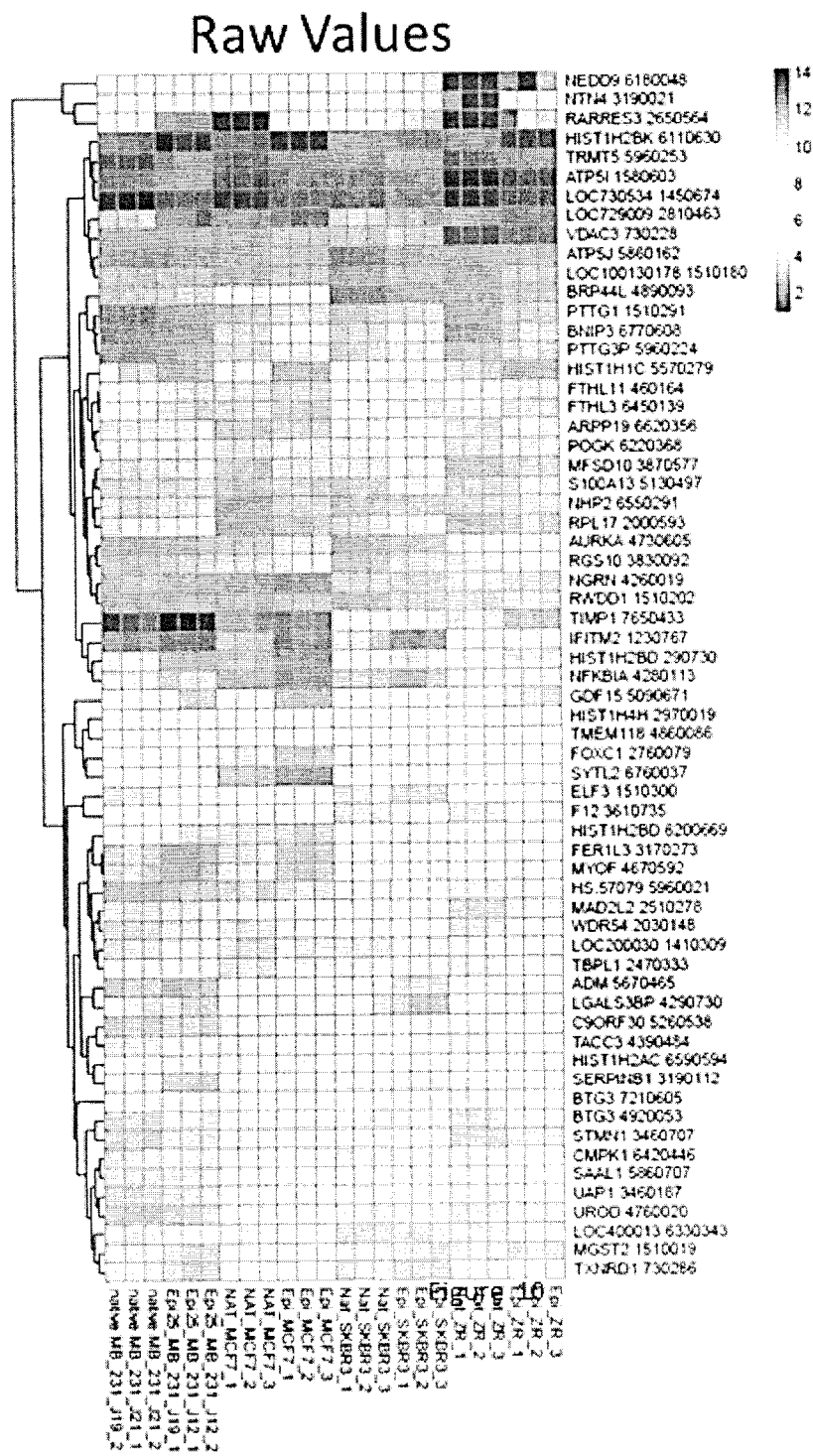
Figure 10B:
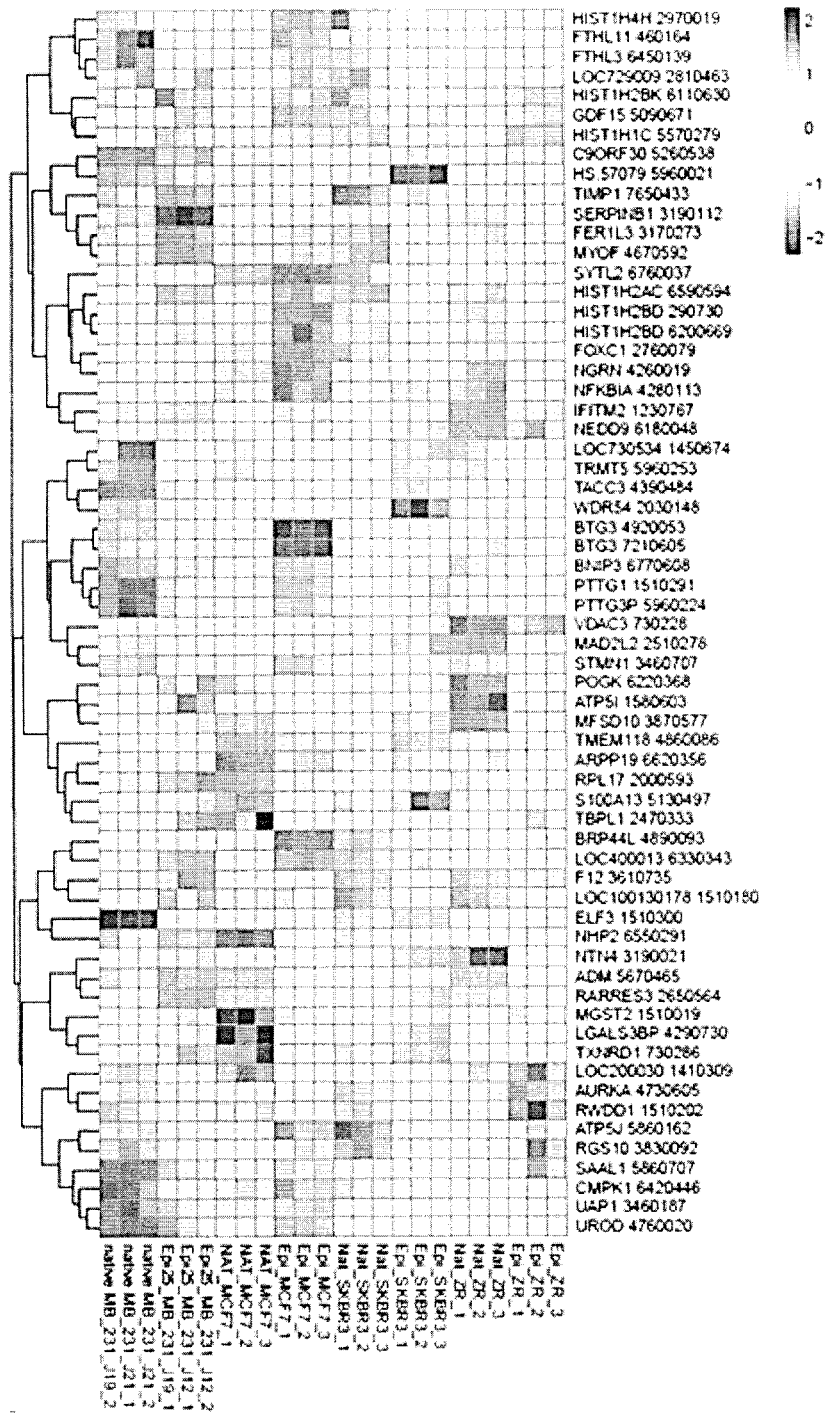
Figure 11:
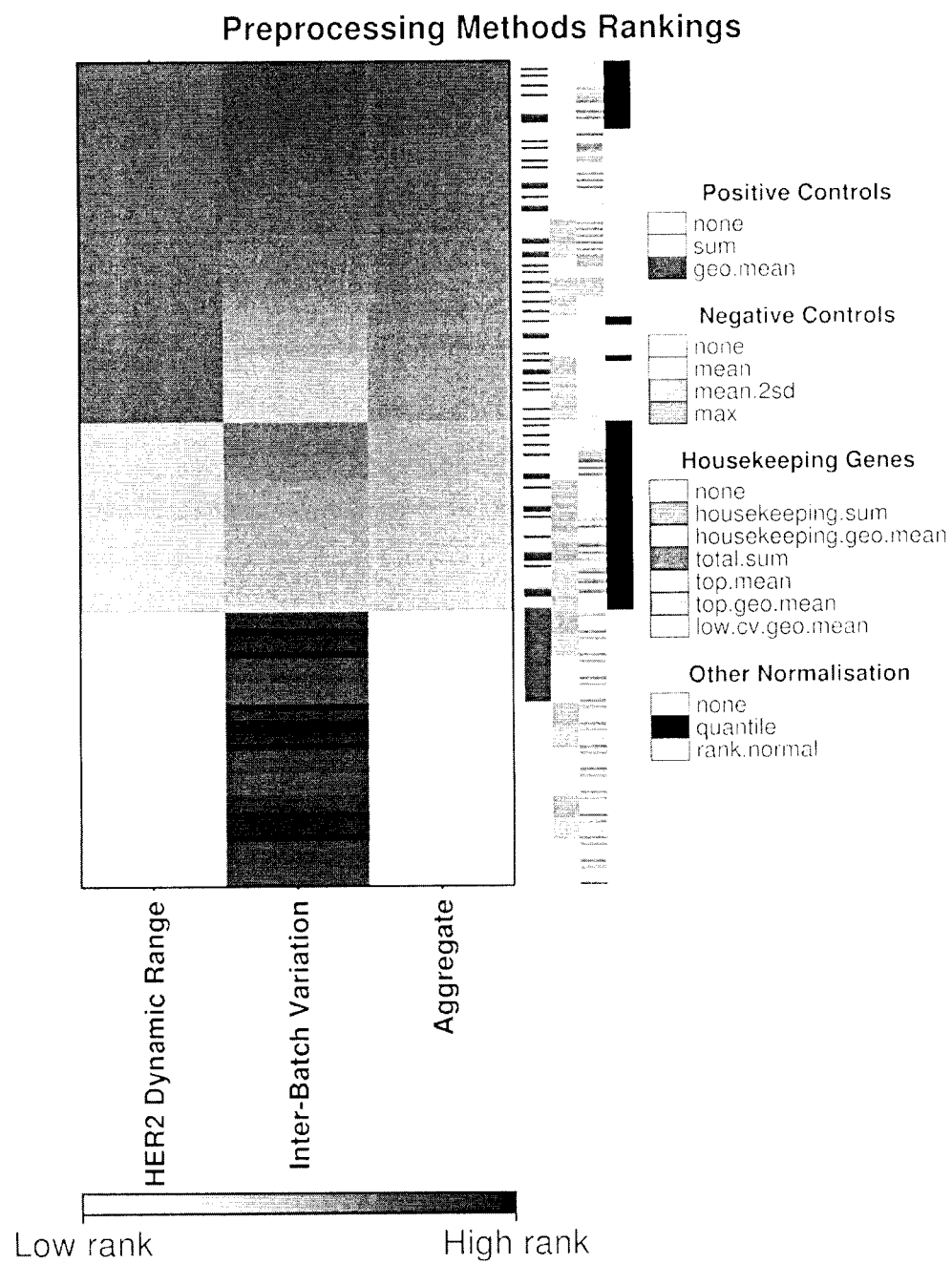
Figure 12:
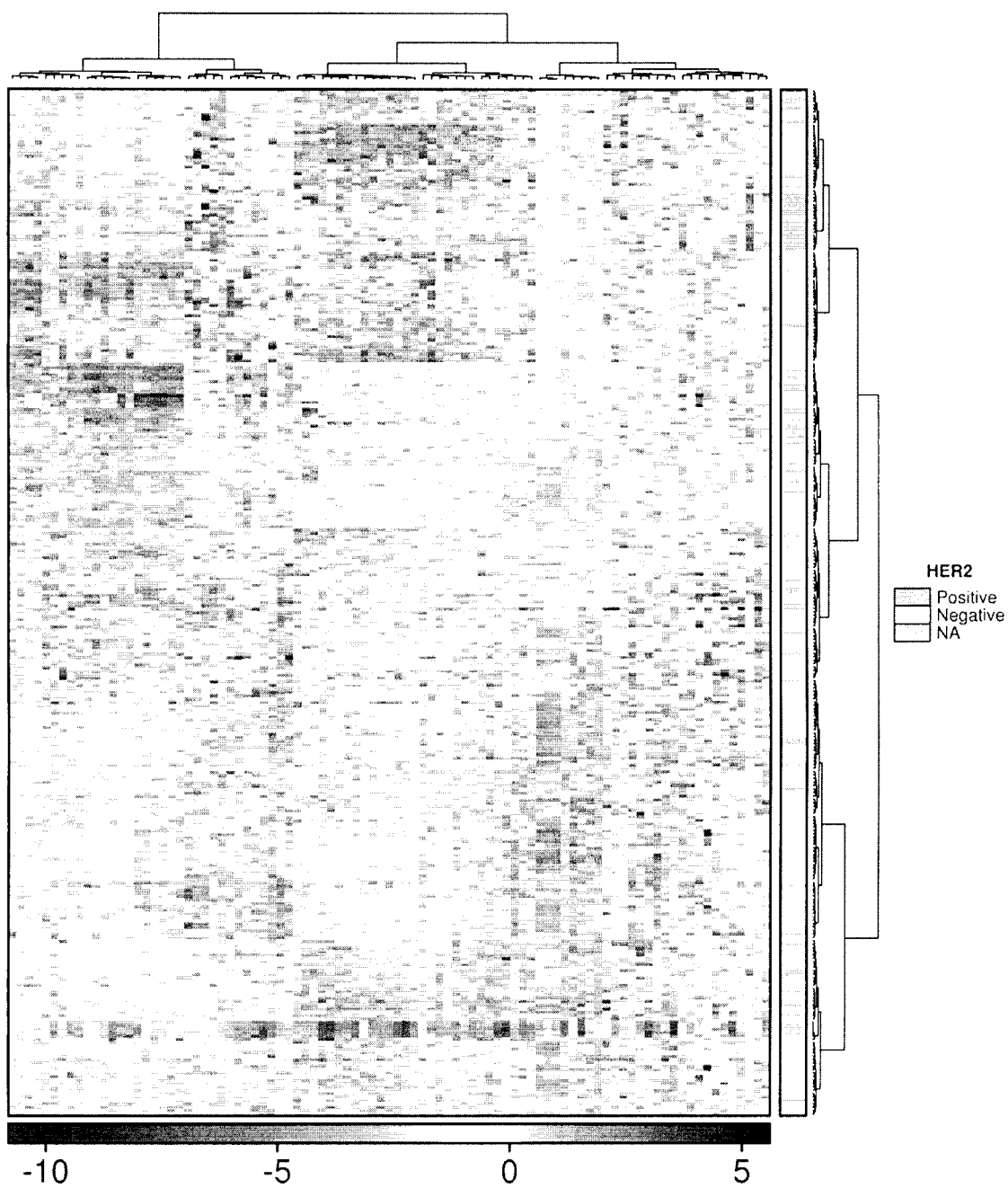
Figure 13:
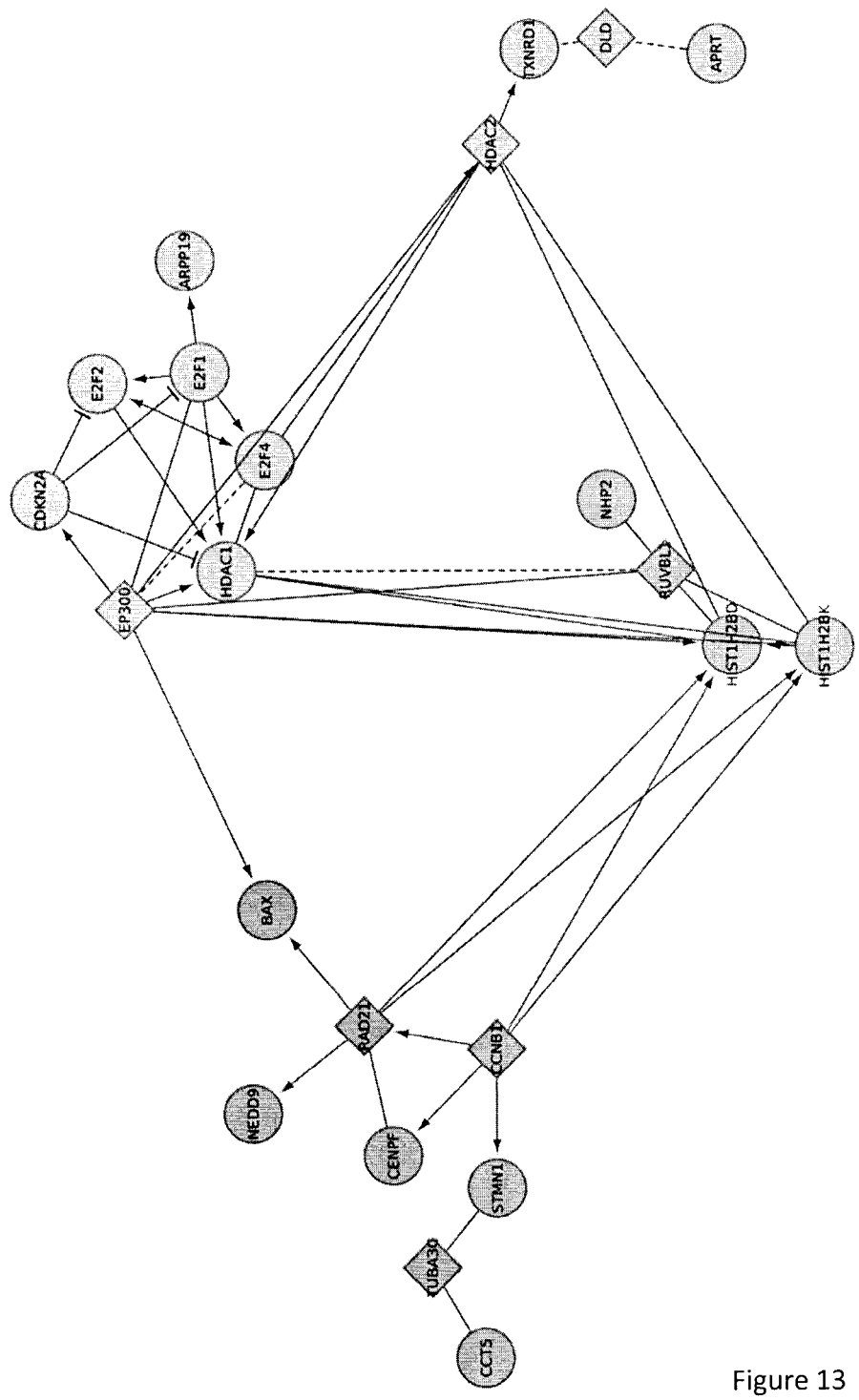
Figure 14:
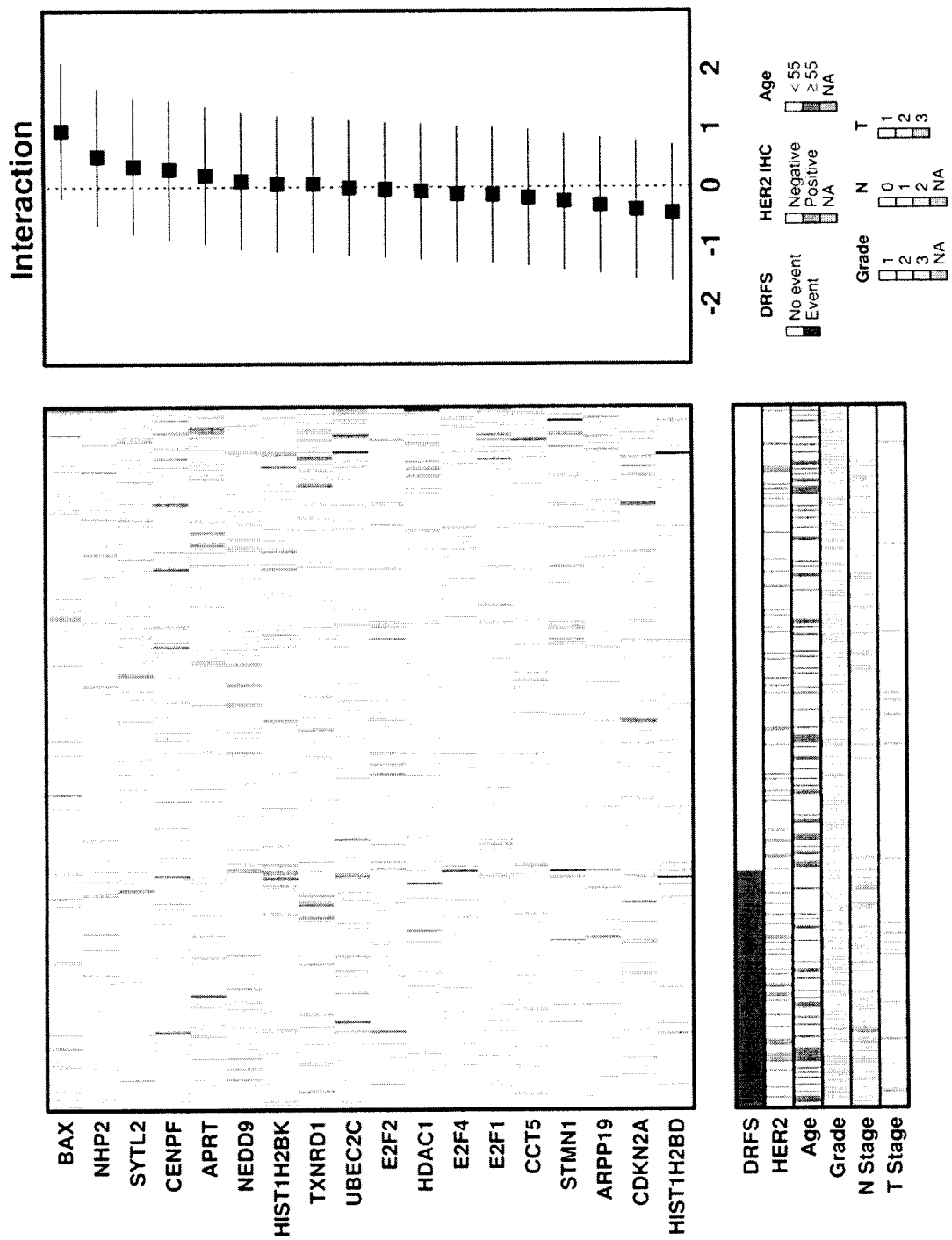

The BR9601 trial recruited 374 pre- and post-menopausal women with completely excised, histologically confirmed breast cancer and a clear indication for adjuvant chemotherapy. Patients were randomized between 8 cycles of CMF (i.v. cyclophosphamide 750 mg/m$^2$, methotrexate 50 mg/m$^2$ and 5-fluorouracil 600 mg/m$^2$) every 21 days, and E-CMF (4 cycles of epirubicin 100 mg/m$^2$ every 21 days followed by 4 cycles of the same CMF regimen) (Poole et al. 2006)(FIG. 8). The protocol was approved by central and local ethics committees, and each patient provided written informed consent prior to randomization. For the current analysis, tissue blocks were retrieved and RNA was extracted. The primary outcomes of the BR9601 study were RFS and OS, although distant relapse-free survival was also reported (Poole et al. 2006).

Cell Culture

Breast cancer cell lines (MDA-MB-231, MCF7, ZR-75-1, SKBR3) were purchased from ATCC and cultured in DMEM (except SKBR3, cultured in RPMI) supplemented with 10% heat-inactivated fetal bovine serum and 1% L-glutamine (Gibco, Burlington, Canada). Epirubicin-resistant cell lines were generated by exposing native cells to increasing concentrations of epirubicin with an initial concentration set at 0.5 nM. Resistance was defined when $IC_{50}$ value superseded the $IC_{50}$ value of the corresponding native cell line, and resistant cells could not tolerate further increase in drug concentration. Drug resistance and cross resistance were determined by exposing cells to drug concentrations ranging from 0.3-3000 nM for 72h. Cell viability was determined by Cell Counting Kit-8 (CCK-8, Dojindo, Cedarlane, Burlington, Canada). $IC_{50}$ were calculated in Graph Pad Prism5.

Flow Cytometry

For cell cycle, cells were synchronized by the double-thymidine block (Whitfield et al. 2000) and incubated with DMSO or epirubicin doses established for each cell line: 25 nM for MDA-MB-231, 30 nM for MCF7, 15 nM for SKBR3, 10 nM for ZR-75-1. Cells were collected at 48h, fixed with 80% ethanol and incubated with 2 mg/ml RNase A and 0.1 mg/ml propidium iodide (both from Sigma, Oakville, Canada) prior to analysis. For apoptosis experiments, cells were treated with DMSO or epirubicin at concentrations described above, and collected at 72h for staining with Annexin V apoptosis-detection eFluor450 (eBioscience, San Diego, USA). Data were collected by FACSCanto II and FACSDiva (BD Biosciences, Mississauga, Canada) and analyzed by FlowJo (Treestar, Ashland, USA).

Proliferation

Cells were cultured in the presence or absence of epirubicin for up to 96h (see Flow Cytometry for epirubicin concentrations). Cells were collected at 24, 48, 72 and 96 hours and counted by ViCell (Beckman Coulter, Mississauga, Canada). Data were analyzed in GraphPad Prism5 software.

Microarray

Illumina Human HT-12-V4 Bead Chips were used for the whole genome microarray analysis by the UHN Microarray Centre, Toronto, Canada. Total RNA was extracted with the RNeasy Mini kit (Qiagen, Toronto, Canada) and used for profiling gene expression changes. Raw data were normalized with the R3.0.0 lumi package using Simple Scaling Normalization; the 10% most variable probes were retained for differential analysis using the genefilter package. Differentially expressed probes were identified using limma with a Benjamini-Hochberg corrected P-value cutoff of 0.05.

Network-Based Analysis

To identify functionally relevant modules, genes demonstrating consistent directionality of significant expression changes were analyzed using the Cytoscape Reactome Functional Interaction (FI) plugin in Cytoscape 2.8.3. Symbols were loaded as a gene set and interactions from the FI network 2012 version, including FI annotations and linker genes. Network modules were identified using spectral clustering and Pathway Enrichment computed for each module using the Reactome FI plugin functions. Reactome pathways exhibiting FDR values <0.01 were considered enriched.

Pharmaceutical Inhibitors

All inhibitors were provided by the Drug Discovery group at the Ontario Institute for Cancer Research (OICR, Toronto, Canada). Cells were seeded at 1000-1500 cells/well into 384-well plates (Greiner, Mississauga, Canada). After 24h, resistant cells were exposed to epirubicin at the selection doses established (see Flow Cytometry), then exposed to HDACi dissolved in DMSO in 12 concentrations ranging from 0.0026-10 µM using D300 digital compound dispenser (HP/Tecan, San Jose, USA); DMSO concentration did not exceed 0.5% in the final drug solution. After 72h, the effects of inhibitors were determined using CellTiter-Glo Luminescent Cell Viability Assay (Promega, Madison, USA) and the Wallac EnVision 2104 Multilabel Reader (Perkin-Elmer, Woodbridge, Canada). Raw data were normalized to negative (media) and positive (20 µM staurosporine) controls and analyzed in GraphPad Prism5.

Quantitative RT-PCR

RNA was isolated from cultured cell lines using RNeasy Mini Kit (Qiagen, Toronto, Canada). A total of 20 ng of RNA was analysed using TaqMan Gene Expression Assays (HIST1H2BD-Hs00371070_m1; HIST1H2BK-Hs00955067_g1; HIST1H2AC-Hs00185909_m1) and EXPRESS One-Step Superscript qRT-PCR universal kit according to manufacturer's protocol (Life Technologies, Burlington, Canada). Reactions were run using Applied Biosystems Viia 7 real-time PCR instrument and software (Life Technologies, Burlington, Canada); transcript levels were quantified from the standard curve generated from the control, Universal Human Reference RNA samples (Agilent, Mississauga, Canada). Statistical significance was determined using unpaired t-test.

Immunoblotting

Whole cell lysates (WCL) were prepared in RIPA buffer supplemented with Complete Mini protease and PhosSTOP phosphatase inhibitors (Roche, Laval, Canada). For cell line characterization, 10-50 µg of total protein was run on 4-20% Mini-Protean TGX precast gels (Bio-Rad, Mississauga, Canada). For histones, cells were collected in 0.1% NP40-PBS to release nuclei. WCL were prepared by adding equal volume of 2×RIPA buffer, supplemented with 25 units of benzonase nuclease (Sigma-Aldrich, Oakville, Canada) and Complete Mini protease inhibitor cocktail (Roche, Laval, Canada), incubating on ice for 30 minutes and sonicating for 15 minutes with 30-second on-off intervals. Twenty µg of WCL were run on a 12% gel. A list of primary antibodies used in immunoblotting is provided in Table 6. Signals were developed with the BM Chemiluminescence Blotting Substrate POD (Roche, Laval, Canada) and ChemiDoc Imaging System (Bio-Rad, Mississauga, Canada).

RNAi Transfection of ZR75-1 and MDA-MB-231 Resistant Cells

A total of $7 \times 10^4$ ZR75-1 EpiR cells and MDA-MB-231 EpiR cells were transfected with Lipofectamine RNAiMAX (Invitrogen, Canada) and 30 nM siRNAs (Dharmacon, Waltman, USA) targeting HIST1H2AC, HIST1H2BK, or both according to manufacturer's instructions. Negative controls included media only, lipofectamine only, or mock transfection with non-targeting siRNA. RNA was collected at 48h and analyzed by qRT-PCR as described above; $IC_{50}$ values were generated in GraphPad Prism5.

nCounter Codeset and Data Pre-Processing nCounter gene expression codeset included 7 genes within the histone module and 11 additional genes that were identified in Kegg pathways (Kanehisa et al. 2014) as being important for histone function (Table 7); HIST1H2AC was excluded from the codeset since probes cross-hybridized to other genes. All 18 genes were functionally related (data not shown). mRNA codesets were processed on nCounter according to manufacturer's instructions (NanoString Technologies, Seattle, USA). Raw mRNA abundance data were pre-processed using the NanoStringNorm R package. A range of pre-processing schemes was assessed to optimize normalization parameters as previously described (Sabine et al., submitted).

Survival Modelling

To assess whether individual genes are prognostic of survival, each gene was median dichotomized into low- and high-expression groups and univariate Cox proportional hazards models were fit (data not shown). Survival analysis of clinical variables modelled age as binary variable (dichotomized at age >50), while nodal status, pathological grade, ER status and HER2 status were modelled as ordinal variables (FIG. 8B). Tumor size was treated as a continuous variable.

mRNA Network Analysis

The investigators hypothesized that integrating molecular modules could improve residual risk prediction relative to DRFS and OS. For each module the investigators calculated a 'module-dysregulation score' (MDS; Methods), which were used in a univariate Cox proportional hazards model. A stratified 5-fold cross validation approach was applied; models were trained in the training cohort and validated in the k-th testing cohort using 10-year DRFS as an end-point. All survival modelling was performed on DRFS and OS, in the R statistical environment with the survival package (v2.37-7). Treatment by marker interaction term was calculated using Cox proportional hazards model.

mRNA Abundance Data Processing

Raw mRNA abundance counts data were preprocessed using R package NanoStringNorm (v1.1.19). In total, 252 preprocessing schemes were assessed, including the use of six positive controls, eight negative controls and six housekeeping genes (TRFC, TBP, GUSB, TMED10, SF3A1, and PUM1) followed by global normalization (data not shown). The investigators used two criteria to help identify the optimal preprocessing parameters as previously described (Sabine et al., submitted). First, each of the 252 combinations of preprocessing schemes was ranked based on their ability to maximize Euclidean distance of ERBB2 mRNA abundance levels between HER2-positive and HER2-negative patients. For robustness, the entire process was repeated for 1 million random subsets of HER2-positive and HER2-negative samples for each of the preprocessing schemes. Second, the investigators included 5 replicates of an RNA pool extracted from randomly selected anonymized FFPE breast tumour samples; the rationale here was to assess each of the different preprocessing schemes for their inter-batch variation and rank them as previously described (Sabine et al. submitted). For this evaluation, a mixed effects linear model was used and residual estimate was used as a metric for inter-batch variation (R package: nlme v3.1-120). Lastly, the investigators estimated the cumulative ranks using Rank-Product (Breitling et al. 2004) based on the two criteria and identified the optimal pre-processing scheme as using geometric mean derived from the top 75 expressing genes for sample content followed by quantile normalisation (data not shown). No samples were removed after QAQC. Six samples were run in duplicates, and their raw counts were averaged and subsequently treated as a single sample.

Module Dysregulation Score (MDS)

As previously described (Sabine et al. submitted, Haider et al., submitted), predefined functional modules were scored using a two-step process. First, weights (β) of all the genes were estimated by fitting a multivariate Cox proportional hazards model and were obtained from the treatment by marker interaction term (Training cohort only). Second, these weights were applied to scaled mRNA abundance profiles to estimate per-patient module dysregulation score using the following equation 1:

$$MDS = \sum_{i=1}^{n} \beta X_i \quad (1)$$

where n represents the number of genes in a given module and $X_i$ is the scaled (z-score) abundance of gene i. MDS was subsequently used in the multivariate Cox proportional hazards model alongside clinical covariates.

Survival Modelling

Using a stratified 5-fold cross validation approach, MDS profiles (equation 1) of patients within each training set were used to fit a univariate Cox proportional hazards model. The parameters estimated by the univariate model were applied to patient-wise MDS in the testing set of each fold to generate per-patient risk scores. These continuous risk scores were dichotomized based on the median threshold derived from each training set, and the resulting dichotomized groups were evaluated through Kaplan-Meier analysis. Models were trained and validated using DRFS truncated to 10 years as an end-point.

Results and Discussion

Generation and Characterization of Epirubicin-Resistant Breast Cancer Cell Lines Resistant cell lines generated from epirubicin-sensitive native cell lines MDA-MB-231, MCF7, SKBR3 and ZR-75-1, exhibited 7- to 67-fold increased resistance to epirubicin (FIG. 1). The investigators tested whether epirubicin-resistant cell lines are cross-resistant to doxorubicin, paclitaxel, docetaxel, SN-38 and carboplatin, drugs used in breast cancer clinical trials. All four epirubicin-resistant cell lines were resistant to doxorubicin (FIG. 1B). While MDA-MB-231, MCF7 and ZR-75-1 epirubicin-resistant cells were not taxane-resistant, SKBR3 epirubicin-resistant cells were cross-resistant to both, paclitaxel and docetaxel (FIG. 1B). MDA-MB-231 and SKBR3 cells were cross-resistant to SN-38, whereas MCF7 and ZR-75-1 tolerated only small increases in SN-38 concentrations. None of the cell lines were cross-resistant to carboplatin (FIG. 1B).

Figure 2:
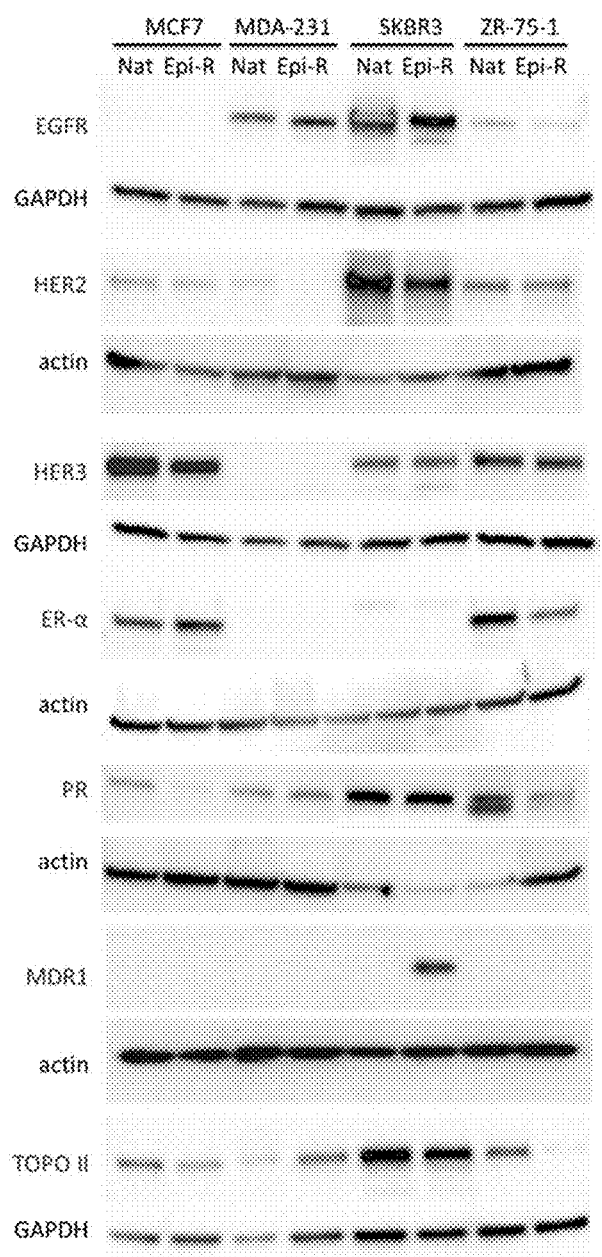
FIG. 2 shows expression of conventional breast cancer biomarkers and select multidrug resistance genes. Cell lysates were prepared in RIPA buffer supplemented with Complete Mini protease inhibitor and PhosSTOP phosphatase inhibitor. 10-50 µg of total protein was run on a 10% gel (MDR1), 4-20% precast gels (EGFR, ER, PgR, TOPOIIα) and Any kD precast gels (HER2, HERS), transferred onto PVDF membrane and developed using chemiluminescence substrate. Nat=native; Epi-R=epirubicin resistant.

Epirubicin-resistant cells showed no marked alterations in EGFR, HER2 and HERS expression levels (FIG. 2); ER and PR expression decreased slightly in epirubicin-resistant ZR-75-1 cells compared to native cells. MDR1 was only upregulated in resistant SKBR3 cells, which may explain their cross resistance to taxanes (FIG. 1B). TOPOIIα expression was downregulated in epirubicin-resistant ZR-75-1 cells (FIG. 2); no changes in MDR or TOPOIIα were observed in epirubicin-resistant MDA-MB-231 and MCF7 cell lines. These results suggest that anthracycline resistance is not MDR-driven for three of four cell lines and that epirubicin-resistant cell lines remained unaltered with respect to the expression of conventional breast cancer biomarkers.

To determine cell-doubling time, the investigators cultured cells with or without epirubicin for up to 96h. In the absence of epirubicin, the native MDA-MB-231 and MCF7 cell populations doubled every 25h and 29h, respectively (Table 2), whereas native SKBR3 and ZR-75-1 cells grew more slowly, doubling every 45h and 50h, respectively. In the presence of epirubicin, doubling time increased 2.8-fold for the MDA-MB-231 (p=0.0371), 2.5-fold for MCF7 (ns), 1.3-fold for SKBR3 (p=0.0494) and 1.9-fold for ZR-75-1 (p=0.0258) for native cells. In contrast to the native cell lines, there were no marked changes in the doubling time of the resistant cells, regardless of whether epirubicin was added (Table 2). Interestingly, in the absence of epirubicin, none of the resistant cells proliferated as rapidly as native cells indicating that epirubicin selection induced permanent changes in resistant cells.

Impaired Apoptosis in Anthracycline-Resistant Cells

To assess the effects of epirubicin on apoptosis, apoptotic cells were scored by flow cytometry after 72h of exposure to epirubicin. The apoptotic index was consistently lower for resistant cells compared to native controls (Table 1). In particular, MDA-MB-231 and SKBR3 resistant cells required a substantially higher concentration of epirubicin (1000 nM) to induce apoptosis; even at this concentration of epirubicin, the apoptotic index was still nearly 50% lower compared to the native cells (Table 1).

Resistant Cell Lines Overcome Epirubicin-Induced G2/M Arrest

Figure 3A:
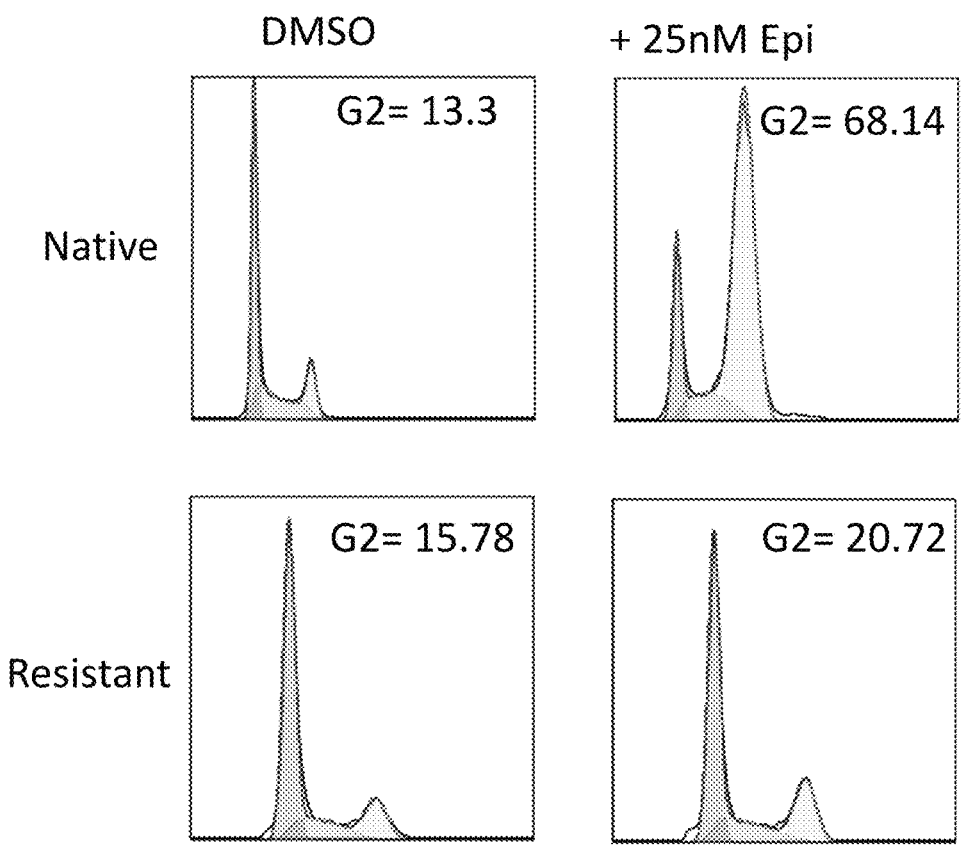
FIG. 3 shows resistant cell lines overcome epirubicin-induced G2/M arrest. (A-D) Cells were synchronized by a double-thymidine block and treated with DMSO or epirubicin at selection doses established for each resistant cell line: 25 nM epirubicin to MDA-MB-231, 30 nM epirubicin to MCF7, 15 nM epirubicin to SKBR3 and 15 nM epirubicin to ZR-75-1. Epirubicin concentration was increased to 100 nM for MCF7 and SKBR3 cells since G2/M block was not observed at the lower doses of epirubicin. Cells were collected at 48h, stained by PI and analyzed by flow cytometry. Debris was gated out.
Figure 3B:
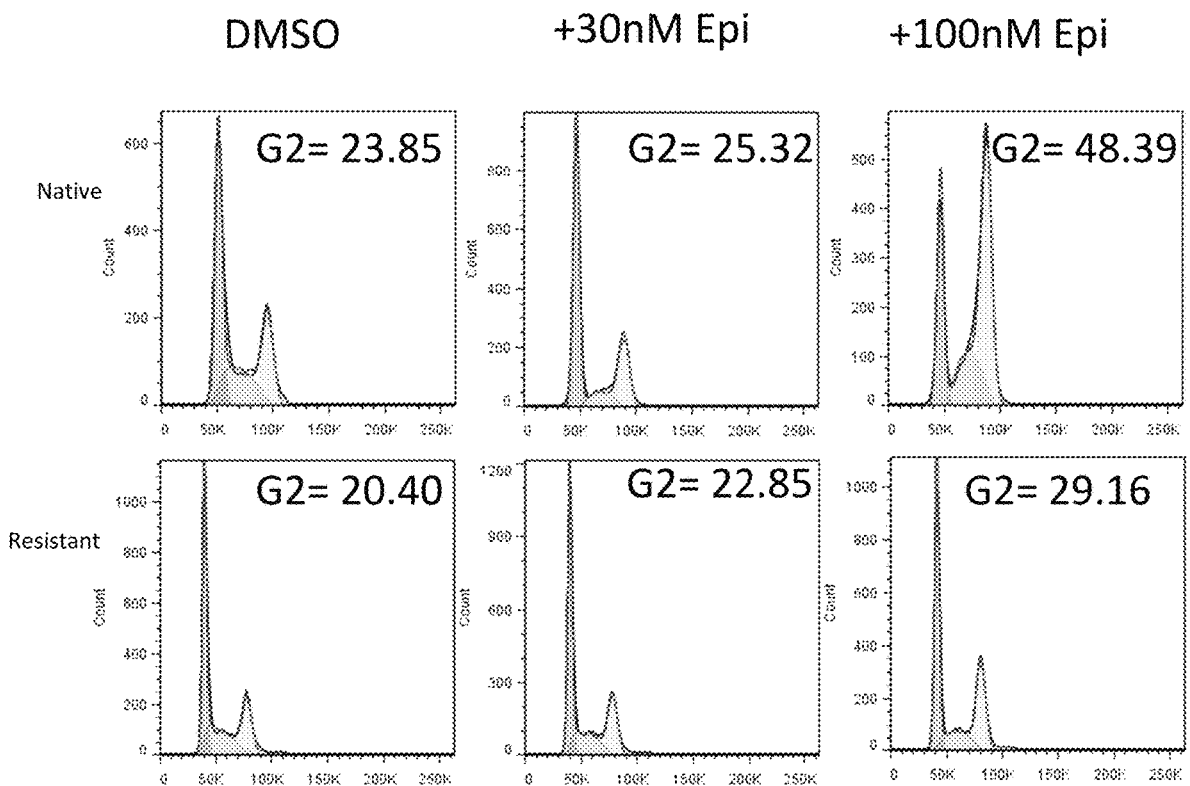
Figure 3C:
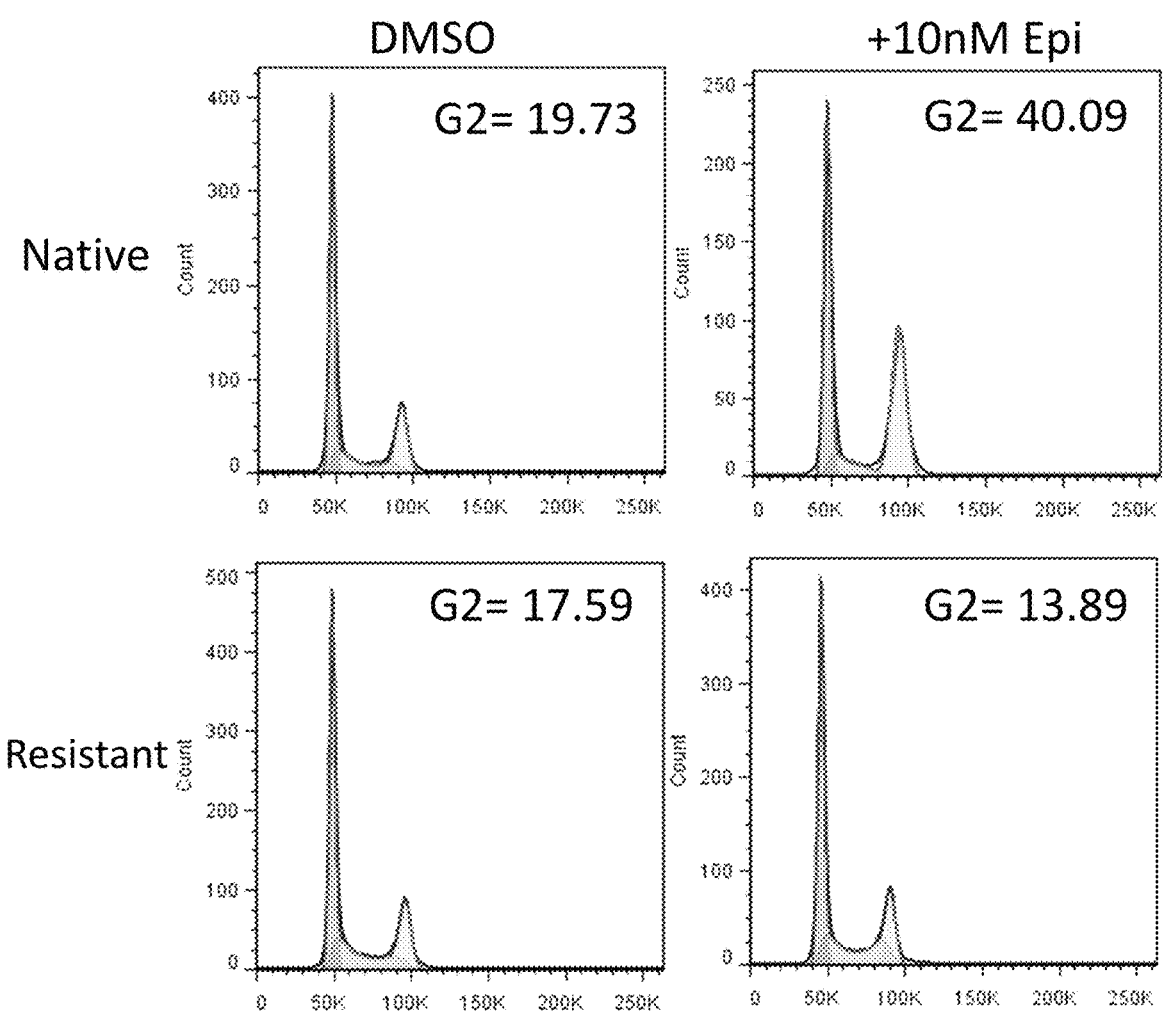
Figure 3D:
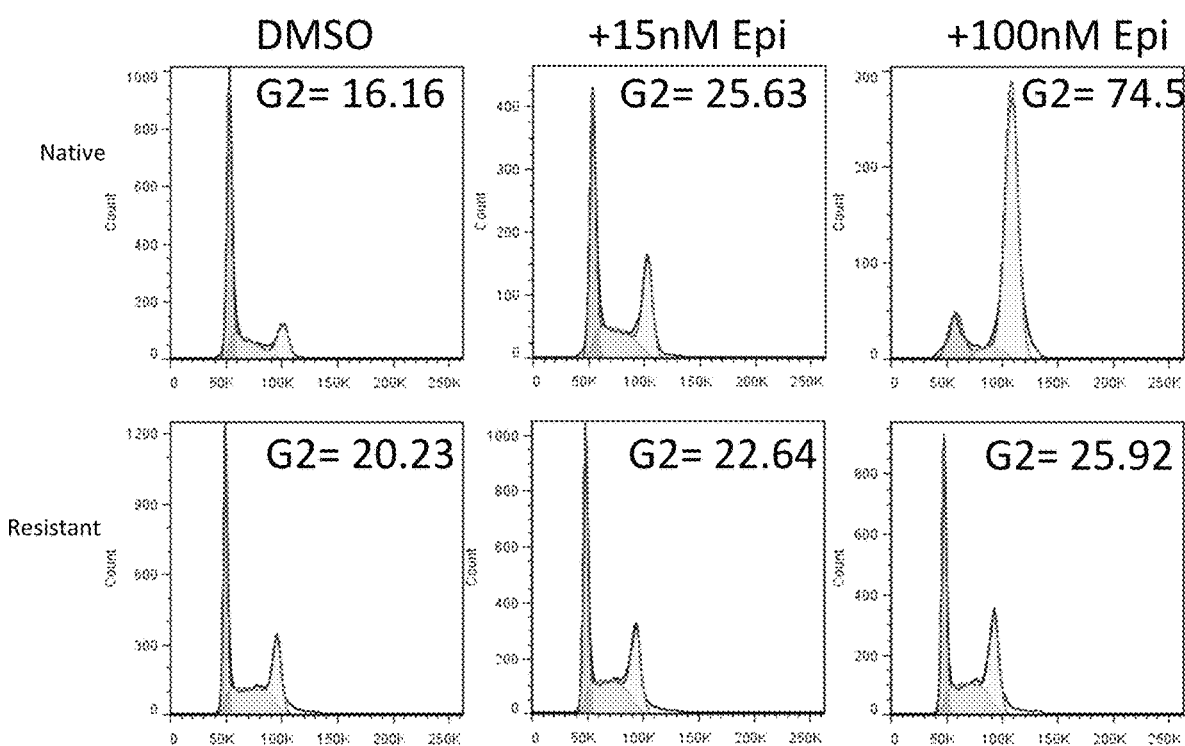

Cells were synchronized prior to exposure to DMSO or epirubicin. All DMSO-treated cell lines progressed through the cell cycle (FIG. 3). When 25 nM and 10 nM epirubicin were added to the MDA-MB-231 and ZR-75-1 cell lines respectively, native cells arrested in G2/M phase whereas resistant cells progressed through (FIG. 3A, C). When 30 nM and 15 nM epirubicin were added to the MCF7 and SKBR3 cell lines respectively, the investigators observed only a modest effect on the cell cycle (FIG. 3B, D); this necessitated increasing epirubicin concentrations to 100 nM at which native cells arrested in G2/M phase, but with minimal effect on the epirubicin-resistant cells (FIG. 3B, D). Therefore, overcoming a G2/M block may be part of the process leading to epirubicin resistance.

Figure 4A:
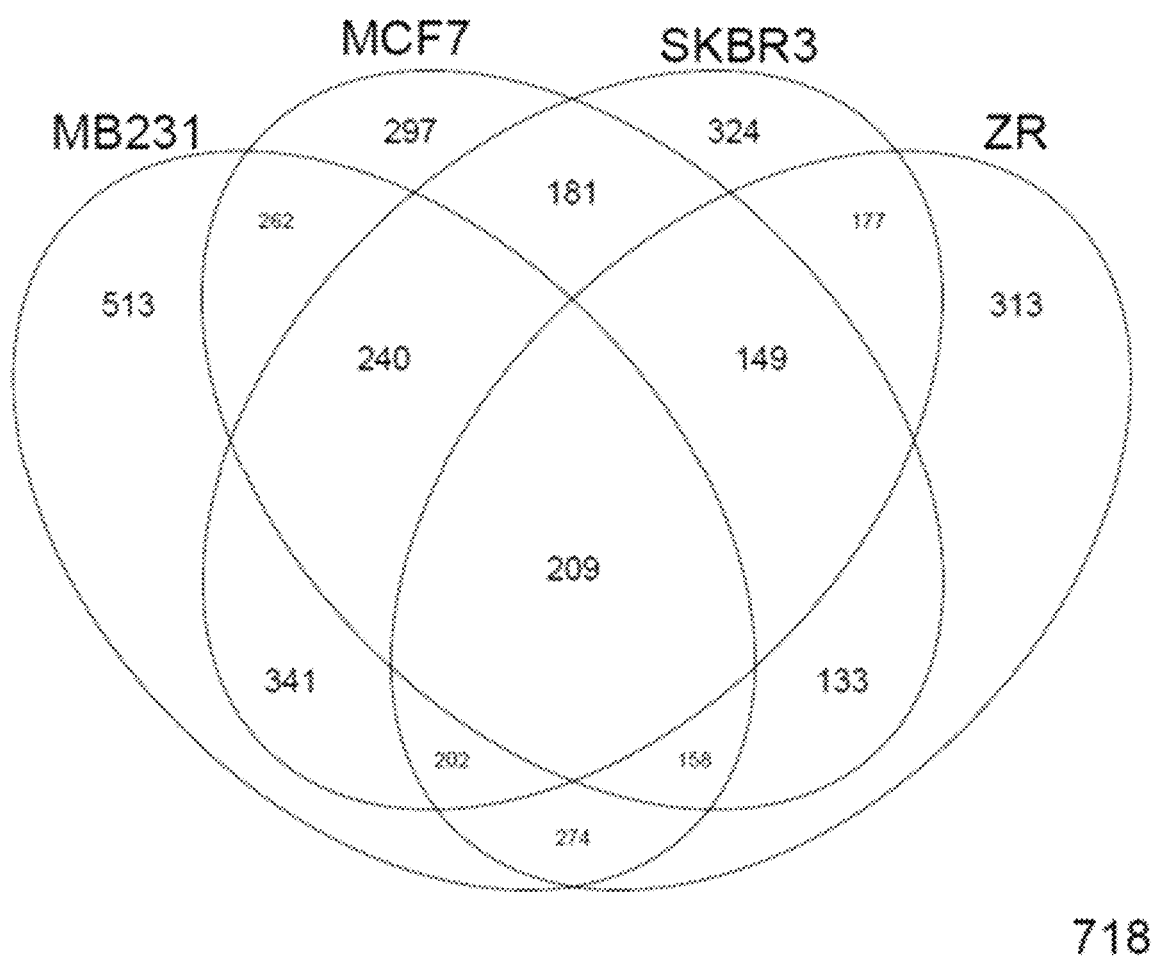
FIG. 4 shows network-based analysis of epirubicin-resistant cell lines. A) Venn diagram of genes with significant changes in expression in breast cancer cell lines. B) Histone module identified from functional interaction network analysis. Coloured rings denote genes demonstrating consistent changes across all 4 lines. Red rings (darker)=upregulated genes, green rings (lighter)=downregulated genes, diamonds=linker genes. C) qRT-PCR performed on RNA isolated from native and epirubicin-resistant cell lines. Bar graphs indicate average quantitative means, while error bars represent SEM. p-values were calculated using unpaired t-test; ns=non-significant. D) Immunoblotting of total H2A and H2B histone proteins in native and epirubicin-resistant cell lines. GAPDH was used as a housekeeping control. E) Reactome pathways significantly enriched within the module shown in panel B.
Figure 4B:
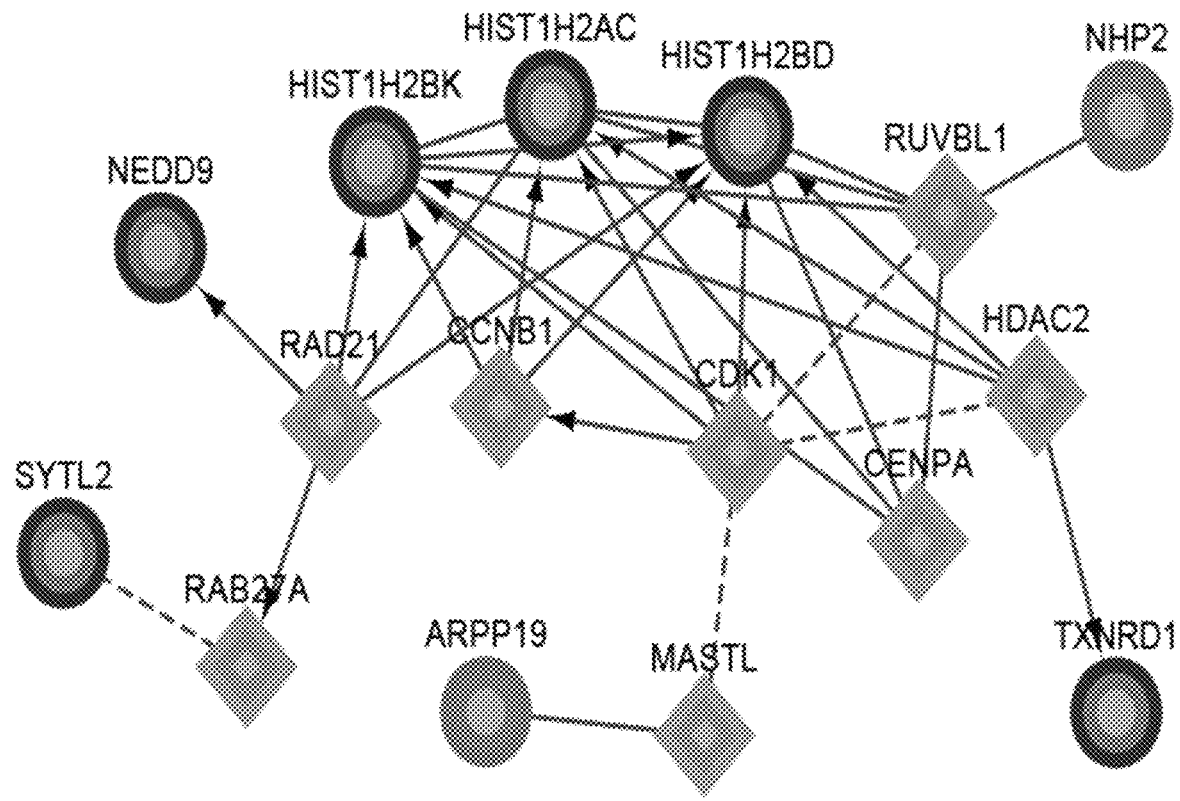

Gene Expression Analyses Identify Histone H2A and H2B Containing Pathways as Potential Functional Drivers of Epirubicin Resistance Whole genome expression analysis revealed 209 genes in common, differentially expressed between all four pairs of native and epirubicin-resistant cell lines (FIG. 4A). Of these, 61 genes were regulated in the same direction in all four cell lines: 26 genes were consistently upregulated and 35 were consistently downregulated (Table 3, FIG. 4). These 61 genes were used to generate a gene interaction network and identify candidate pathways involved in epirubicin resistance. A minimal set of linker genes was used to connect the network. Identifying clustered genes within the network revealed four modules (data not shown); however, only modules I and II contained significantly enriched pathway annotations with a False Discovery Rate (FDR)<0.01. Module I contained three histone genes (HIST1H2AC, HIST1H2BK, HIST1H2BD) and several genes involved in RNA processing and mitosis (FIG. 4B). Importantly, all three histone genes were upregulated in all four cell lines and directly interconnected without linker genes. Within module I, significantly enriched pathways included cell-cycle regulation (FIG. 4E), consistent with our results in FIG. 3. Module II contained three directly connected genes (TACC3, AURKA, NFKBIA) involved in Aurora A kinase signaling; while NFKBIA was upregulated, TACC3 and AURKA were downregulated.

Figure 4C:
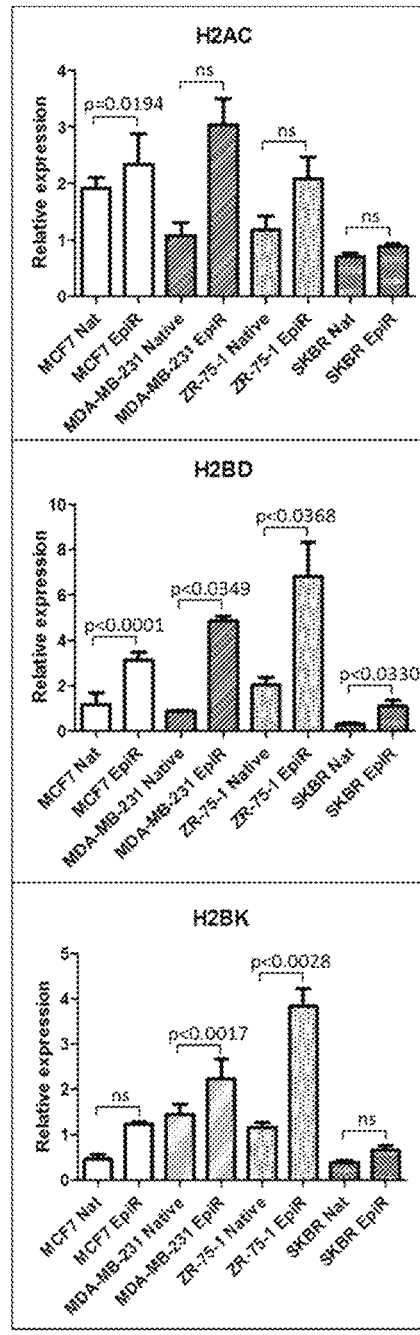
Figure 4D:
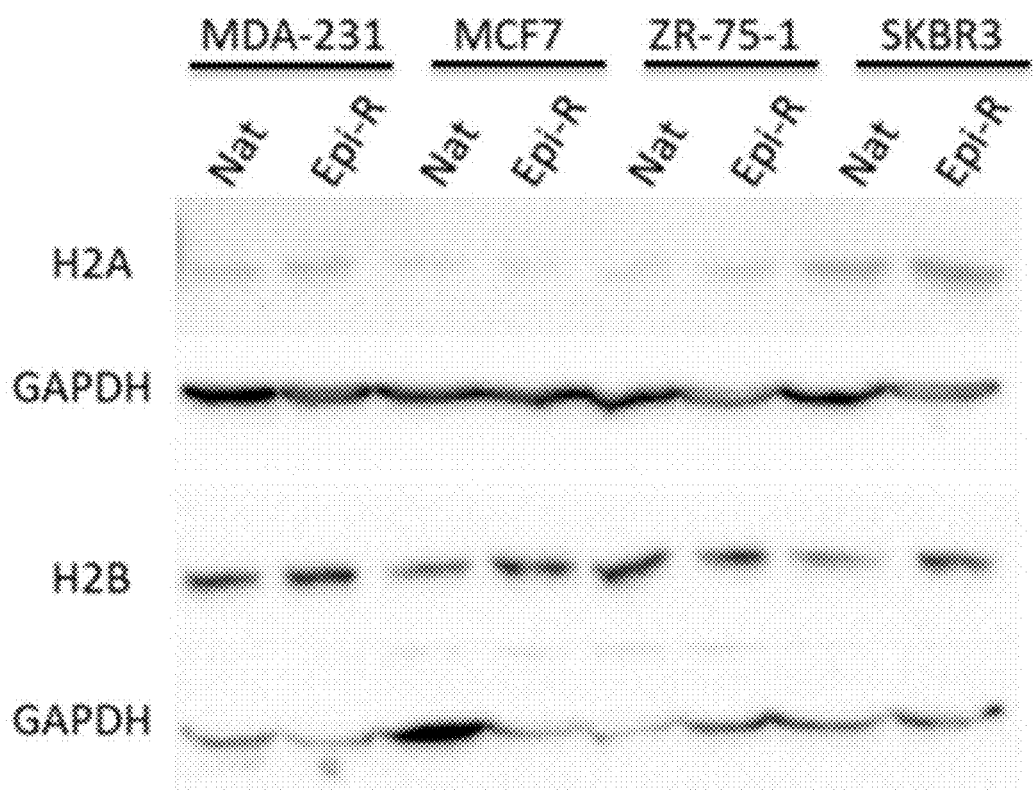

The investigators focused on the histone-containing module 1 since all three histones were upregulated, tightly interconnected without linker genes and implicated in several molecular pathways. Elevated levels of all three histone transcripts were validated by qRT-PCR (FIG. 4C). Since antibodies specific to individual histone variants are not commercially available, the investigators assessed protein expression using pan H2A and H2B antibodies; the investigators observed no difference in the total H2A and H2B levels between resistant and native cell lines (FIG. 4D). Overall, our findings suggest that histone upregulation is a common event associated with epirubicin resistance in breast cancer cells and that histone-related pathways might be functional drivers of epirubicin resistance.

Figure 5:
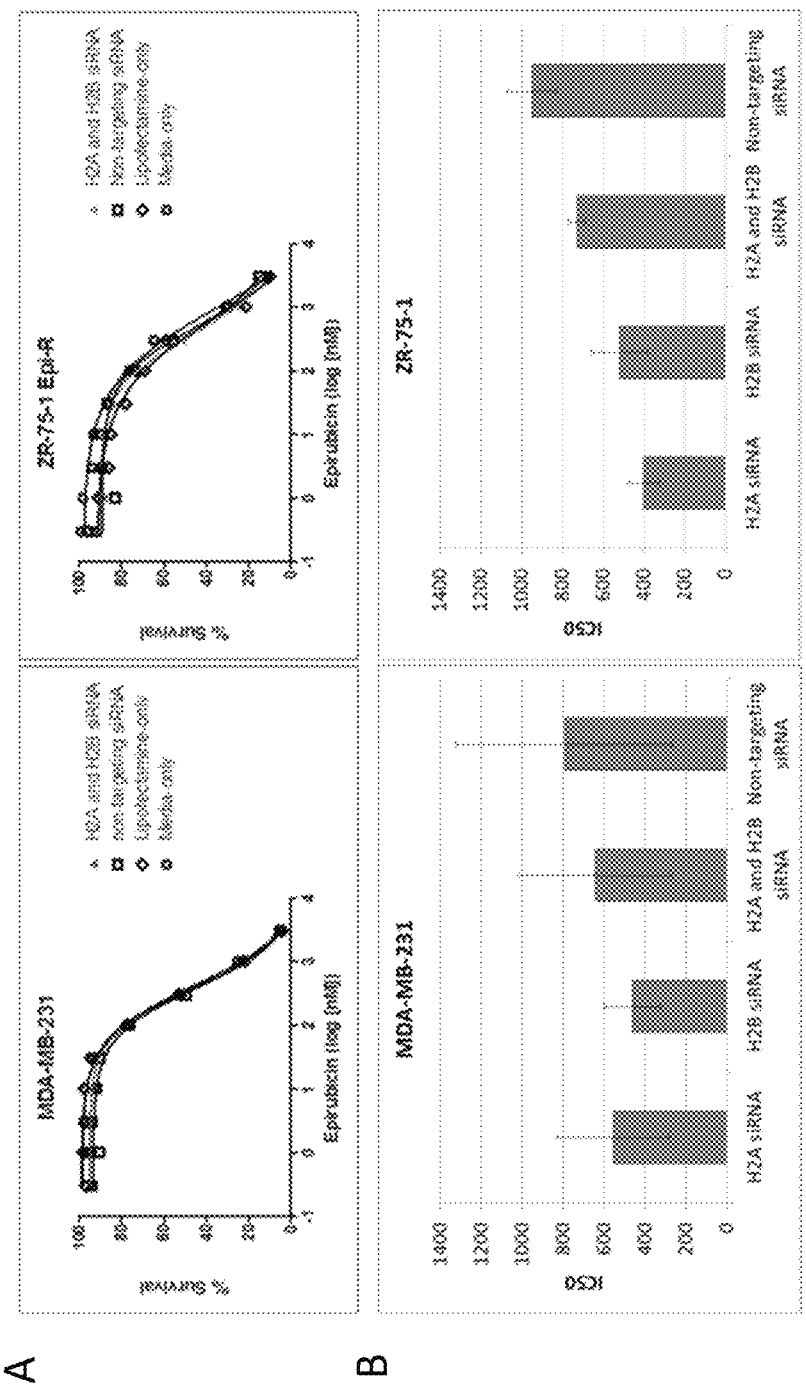
FIG. 5 shows histone gene knockdown is not sufficient to resensitize breast cancer cells to epirubicin. A total of $7 \times 10^4$ ZR75-1 EpiR cells and MDA-MB-231 EpiR cells were transfected with 30 nM of each siRNAs (Dharmacon, Waltman, USA) targeting HIST1H2AC and HIST1H2BK (individual knockdowns not shown for simplicity). Negative controls included media only, lipofectamine only or mock transfection with non-targeting siRNA. Percent gene expression knockdown is shown in Table 4. B) $IC_{50}$ values were generated using non-linear regression analysis and average values of two independent experiments were graphed. Error bars represent standard deviation.

Histone Gene Knockdown is not Sufficient to Resensitize Breast Cancer Cells to Epirubicin The investigators performed a series of gene knockdown experiments in MDA-MB-231 and ZR-75-1 resistant cells in which HIST1H2AC, HIST1H2BK, or both were silenced prior to exposing cells to epirubicin. HIST1H2BK, rather than HIST1 H2BD, was selected because high transcript levels of this variant were associated with poor survival of breast cancer patients in our in silico analysis (data not shown; for online tool see reference (Gyorffy et al. 2010)). Following gene knockdown, a proliferation assay was performed to assess whether resistant cells were resensitized to epirubicin. A decrease in histone transcripts was confirmed by qRT-PCR and summarized in Table 4. Interestingly, transient knockdown of either histone alone, or both, did not re-sensitise cell lines to epirubicin (FIG. 5 and data not shown). The results suggest that downregulation of one or two histone genes is insufficient to reverse epirubicin resistance and that future approaches may have to target multiple molecules within the histone module.

Histone Module is a Clinical Marker of Anthracycline Sensitivity

The prognostic significance of the 18-gene histone module was tested on the entire BR9601 clinical cohort, irrespective of allocated adjuvant chemotherapy. High histone module expression was associated with reduced distant relapse free survival (DRFS; HR: 2.64, 95% CI 1.7-4.09, p=1.44×10$^{-5}$), indicating that elevated histone module is prognostic for poor survival.

Figure 6A:
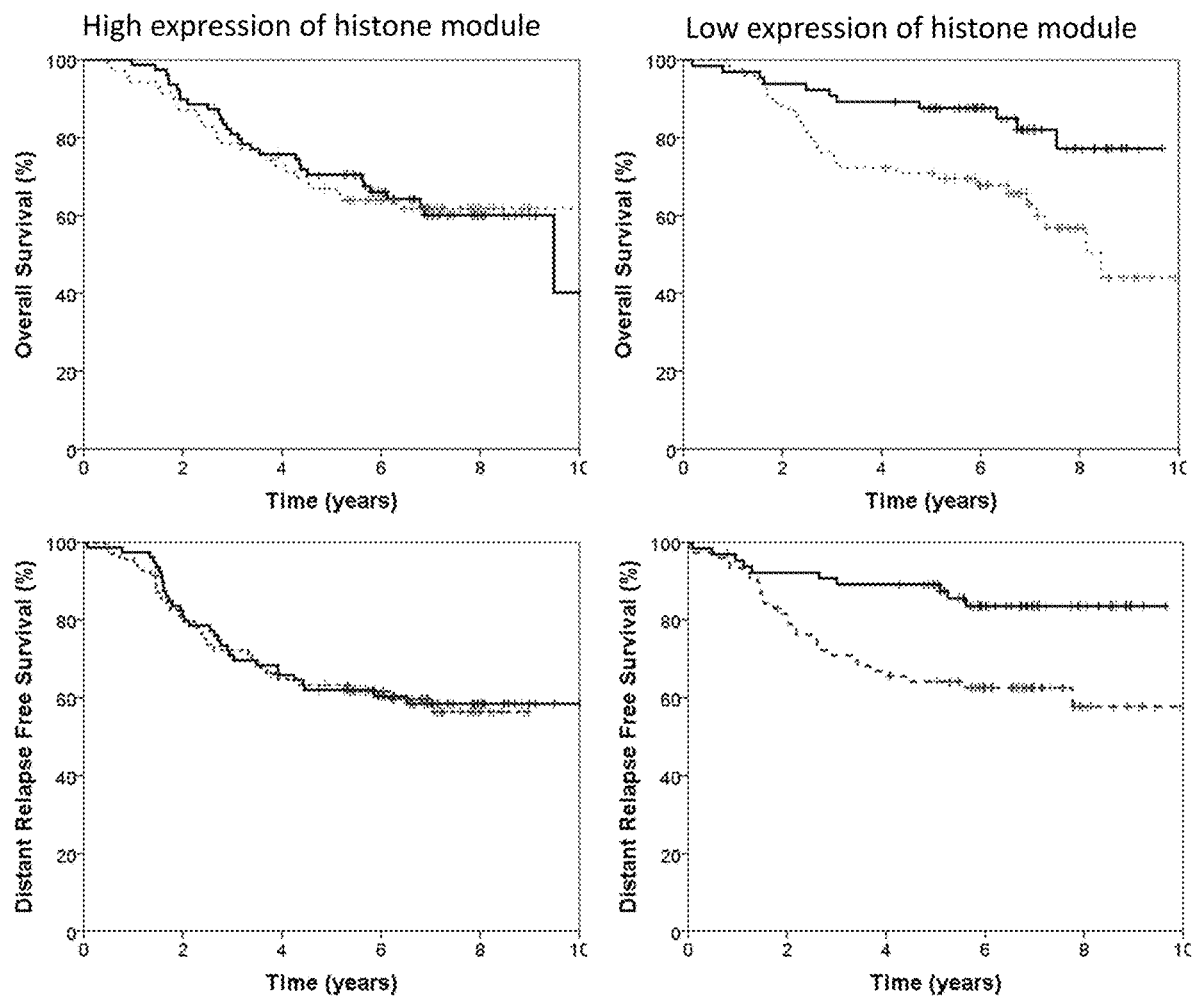
FIG. 6 shows histone module is a biological marker for anthracycline therapy. High expression and low expression of histone module were tested for association with distant recurrence free survival (DRFS) and overall survival (OS) in BR9601 trial in which patients were treated with standard chemotherapy (CMF) or anthracycline-containing chemotherapy (E-CMF). A) DRFS and OS for patients treated with E-CMF versus CMF split into high or low histone gene expression groups. B) Multivariate, treatment by marker analysis after adjustment for HER2 status, ER status, nodal status, grade and age. HR=hazard ratio, CI=confidence interval.

Next, the investigators analysed the differential effects of the histone module on breast cancer-specific overall survival (OS) and DRFS between patients in the BR9601 trial receiving an anthracycline (E-CMF) and those given CMF alone by assessing hazard ratios and treatment by marker interactions. Patients whose tumours had low gene expression had an increased OS (HR: 0.38, 95% CI 0.19-0.76, p=0.005) when treated with E-CMF compared with patients treated with CMF alone; conversely, there was no apparent differential benefit of E-CMF vs CMF in patients with high histone module expression for OS (HR: 0.97, 95% CI 0.57-1.64, p=0.91) (FIG. 6A). Similarly, patients whose tumour had low histone module expression had an increased DRFS (HR: 0.35, 95% CI 0.17-0.73, p=0.0048) when treated with E-CMF compared with patients treated with CMF alone (FIG. 6A); there was no apparent differential benefit of E-CMF vs CMF in patients with high histone module expression for DRFS (HR: 0.96, 95% CI 0.58-1.59, p=0.87). In a multivariate analysis, after adjustment for HER2 status, nodal status, age, grade and ER status, treatment by marker interaction showed no statistical difference for OS (HR:0.50, 95% CI 0.19-1.31, p=0.159); the likelihood of DRFS remained, however, low among patients with low histone module gene expression than in patients with high expression (HR:0.35, 95% CI 0.13-0.96, p=0.042) (FIG. 6B).

HDAC Inhibitors Induce Cytotoxicity in Epirubicin-Resistant Cells Lines

Figure 7A:
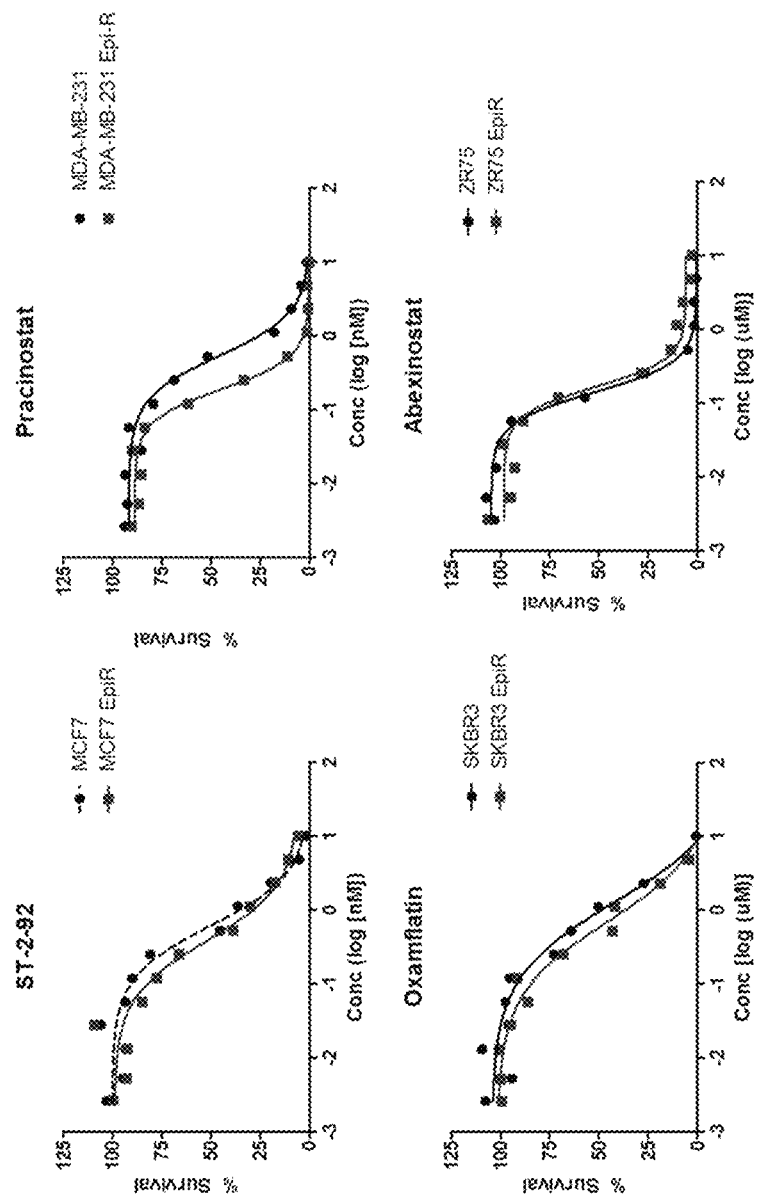
FIG. 7 shows HDAC inhibitors induce cytotoxicity in epirubicin-resistant cells lines. A) Examples of inhibitors that were more cytotoxic for resistant-cell lines (pracinostat for MDA-MB-231, ST-2-92 for MCF7, oxamflatin for SKBR3) or had no selective differences between the native and epirubicin-resistant cells (ZR-75-1). $IC_{50}$ values are shown in Table 5. B) Working models of molecular mechanisms involved in epirubicin resistance. There are three proposed mechanisms by which HDACi sensitize cells to epirubicin: 1) by transcriptional activation of repressors and pro-apoptotic genes, 2) by repression of resistance genes and 3) due to increased accessibility to DNA.

Gene expression analysis identified the histone module as significantly altered and possibly functionally required for epirubicin resistance. Consequently, the investigators tested whether alteration of histone activity may sensitize cells to epirubicin using histone deacetylase (HDAC) inhibitors, which reverse histone hypo-acetylation and permit transcriptional activation. Twenty four HDAC inhibitors (HDACi) were tested against the native and epirubicin-resistant cell lines; for resistant cell lines, all inhibitors were tested in the presence of selection doses of epirubicin. Positive hits were defined as compounds that exhibited cytotoxicity in at least 50% of population and had an IC$_{50}$<5 µM in all eight cell lines. As a result, 14 HDACi were cytotoxic to all native and epirubicin-resistant cells lines (Table 5). Importantly, three of four resistant cell lines were more sensitive to epirubicin than native cells when several HDACi were supplied. For instance, pracinostat was more cytotoxic for MDA-MB-231, ST-2-92 for MCF7 and oxamflatin for SKBR3 epirubicin-resistant cells compared to native cell lines (FIG. 7A); no differences were observed between native and epirubicin-resistant ZR-75-1 cell for any cytotoxic HDACi tested (FIG. 7A). Since inhibitors target different HDAC's and none of the inhibitors ubiquitously resensitized all four resistant cell lines (Table 5), it appears that different classes of HDAC's are involved in anthracycline resistance, possibly in breast cancer-subtype specific manner. Collectively, our data reveal a previously unrecognized role of histones and suggests that H2A and H2B histones are involved in clinical anthracycline resistance.

Anthracycline resistance represents a major obstacle to the effective treatment of women with breast cancer. Although various mechanisms may contribute to anthracycline resistance, including activation of drug transporters, reduced activity of TOPOIIα and inhibition of apoptosis, the majority of the molecular mechanisms involved in clinical drug resistance remain unknown. Using a panel of four paired cell lines representative of the major molecular subtypes of breast cancer the investigators have shown that deregulation of histones involved in chromosome maintenance, epigenetic pathways, cell division and gene regulation are observed consistently in epirubicin resistant cell lines. This observation was then validated clinically in the BR9601 adjuvant clinical trial cohort.

The dysregulation of histones is associated to increased cell cycle progression, specifically the release of a G2/M cell cycle block in the presence of epirubicin, and a reduction in apoptotic cell death. Interestingly, transcriptional knockdown of the two histone variants contributing to the dysregulation signature failed to resensitize cells to anthracycline, possibly due to two reasons. First, although the transcript levels were reduced by 6-53%, it is possible that the protein levels remained unchanged during our experimental window. Second, even if the protein levels were sufficiently diminished, it is still possible that other histone variants functionally substituted for the HIST1H2AC and HIST1 H2BK since there are nine H2A and eleven H2B non-allelic histone variants (Bonenfant et al. 2006). Importantly, using small-molecule inhibitor screen the investigators have shown that drugs directly targeting HDAC function do reverse epirubicin resistance.

Epirubicin-resistant cell lines were generated by exposing native, non-resistant cell lines to increasing concentrations of epirubicin. Interestingly, only a single cell line, SKBR3, upregulated drug transporters and this was associated with cross resistance to taxanes. Previously, Hembruff et al. (Hembruff et al. 2008) developed epirubicin-resistant MCF-7 cells and established that a specific selection dose must be surpassed in order to activate drug transporters; for MCF-7, this critical threshold concentration was around 30 nM (19). Although this concentration is identical to the selection dose of our resistant MCF-7 cells, MDR was not upregulated, suggesting a stochastic nature of molecular events that take place en route to drug resistance. Importantly, it indicates that there exist previously unappreciated MDR-independent mechanisms of resistance that should be evaluated for clinical relevance.

Our study revealed that one of those mechanisms involves upregulation of H2A and H2B genes and several pathways, including epigenetic and cell cycle pathways. H2A and H2B histones form octamers with H3 and H4 histones, which participate in packaging of DNA into nucleosomes (Wyrick and Parra 2009). These histones are replication-dependent and cell-cycle regulated, increasing 35-fold in S-phase during DNA replication (Harris et al. 1991). Thus, elevated histone transcript levels may be a consequence of a stalled cell cycle as cells struggle to repair epirubicin-induced DNA damage. However, since resistant cells did not stall, the investigators eliminated the possibility that upregulated histone transcripts were a mere reflection of accumulated mRNA.

Figure 7B:
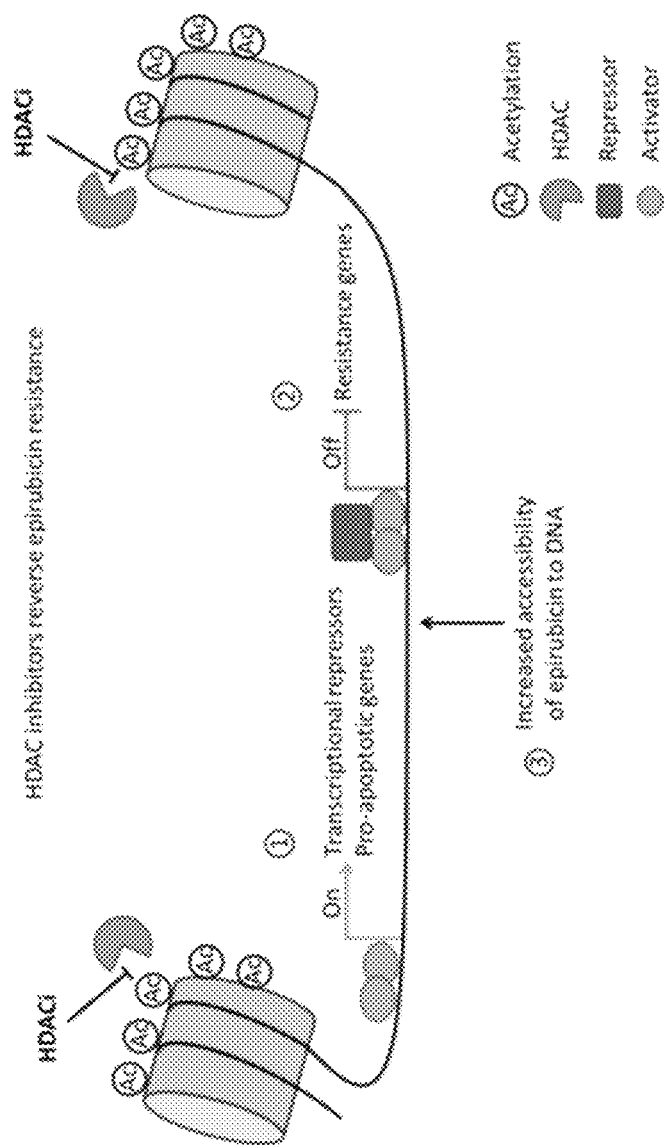

An alternative explanation, supported by the ability of HDACi to sensitize resistant cells to epirubicin, is that upregulation of histones contributed to 1) the activation of resistance pathways, 2) the silencing of molecular pathways that sensitize cells to anthracyclines, and/or 3) a decreased accessibility of epirubicin to DNA. H3 and H4 histones modification patterns strongly associate with either active or repressed gene transcriptional status. Current understanding of H2A and H2B histone modifications is based on studies in yeast and few tumour cell lines; nonetheless, two important features of H2A and H2B histone modifications have been revealed. First, modified sites are acetylated, phosphorylated and ubiquitinated, but not methylated (Parra and Wyrick 2007; Parra et al. 2006; Beck et al. 2006), a modification most commonly observed with H3 and H4 histones. This highlights the appropriate use of HDACi in our study and their potency due to numerous acetylation sites, although this does not eliminate the possibility that the inhibitors were acting on H3 and H4 histones as well. Since acetylated sites on H2A and H2B are associated with transcriptional activation (Parra and Wyrick 2007; Parra et al. 2006), modifying the acetylation pattern may have activated transcriptional repressors and pro-apoptotic genes outlined in our model (FIG. 7B, point 1). Second, the N-terminal end of H2A and H2B histones possesses a repression domain that inactivates gene transcription in approximately 10% of the yeast genome (Parra and Wyrick 2007; Parra et al. 2006), suggesting that these domains could have collaborated with acetylation patterns induced by HDACi to repress genes involved in resistance, such as those involved in cell cycle or apoptosis (FIG. 7B, point 2). Lastly, our model also recognizes that resistance might have been reversed by an increased accessibility of epirubicin to DNA (FIG. 7B, point 3).

Regel et al. (Regel et al. 2012) showed that HDACi panobinostat sensitizes gastric cancer cells to anthracyclines. Our findings are consistent with their study and show that multiple HDACi reverse anthracycline resistance in breast cancer cells. This is an important finding since many of the pharmacological inhibitors tested in our study are in use either as single-agents or as combination therapies in phase II/III clinical trials (Groselj et al. 2013; Wagner et al. 2010; Lee et al. 2012); HDAC inhibitors currently in clinical trials include panobinostat, quisinostat, givinostat, abexinostat, pracinostat, belinostat and mocetinostat (Table 5). Since anthracycline resistance may lead to cross-resistance to taxanes (Guo et al. 2004; Gosland et al. 1996) as it did in one of our resistant cell lines, it may be that taxanes, not anthracyclines, should be used in a first-line treatment (Paridaens et al. 2000). Furthermore, as cancer cells could acquire resistance to HDACi (Lee et al. 2012), sequential therapy involving HDACi, taxanes and anthracyclines will be an important aspect of clinical trial design and medical practice.

The investigators have identified novel pathways containing histone H2A and H2B genes as a mechanism of drug resistance across a spectrum of breast cancer cell lines and validated this finding in the BR9601 adjuvant clinical trial cohort. Furthermore, the investigators have developed a relevant model for studying clinical resistance as low histone expression correlated with better patient outcome. The model system opens avenues to its use for developing and testing novel single or combination, breast cancer therapies In summary, the investigators generated paired native and epirubicin-resistant MDA-MB-231, MCF7, SKBR3 and ZR-75-1 epirubicin-resistant breast cancer cell lines to identify pathways contributing to anthracycline resistance. Native cell lines were exposed to increasing concentrations of epirubicin until resistant cells were generated; characterization of these cells revealed that they were cross-resistant to doxorubicin and SN-38, and had alterations in apoptosis and cell cycle profiles. To identify mechanisms driving epirubicin resistance, the investigators used a complementary approach including gene expression analyses to identify molecular pathways involved in resistance, and small-molecule inhibitors to reverse resistance.

Gene expression analysis identified deregulation of histone H2A and H2B genes in all four cell lines. Histone deacetylase small-molecule inhibitors reversed resistance and were cytotoxic for epirubicin-resistant cell lines confirming that histone pathways are associated with epirubicin resistance. Gene expression analysis of the BR9601 adjuvant clinical trial revealed that patients with low expression of the histone module benefited from anthracycline treatment more than those with high expression (HR: 0.35, 95% CI 0.13-0.96, p=0.042). The present study has revealed a key pathway that contributes to anthracycline resistance and established model systems for investigating drug resistance in all four major breast cancer subtypes. As this process can be targeted with small-molecule inhibitors, it presents a possible means of reversing clinical anthracycline resistance.

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

TABLE 1

Percentages of apoptotic* cells following a 72 h epirubicin treatment

| MDA-MB-231 | DMSO | 1 nM | 25 nM | 1000 nM |
| --- | --- | --- | --- | --- |
| Native | 18 | 17 | 41 | 94 |
| 25 nM-R | 10 | 10 | 8 | 50 |
| MCF7 | DMSO | 1 nM | 30 nM | 1000 nM |
| Native | 32 | 29 | 49 | 77 |
| 30 nM-R | 20 | 24 | 23 | 78 |
| SKBR3 | DMSO | 1 nM | 15 nM | 1000 nM |
| Native | 22 | 26 | 24 | 59 |
| 15 nM-R | 18 | 17 | 17 | 34 |
| ZR-75-1 | DMSO | 1 nM | 10 nM | 1000 nM |
| Native | 36 | 44 | 47 | 71 |
| 10 nM-R | 29 | 28 | 29 | 62 |

*Apoptotic cells = Annexin + Debris and necrotic cells (Annexin v⁻, 7-AAD⁺) were gated out. Percentages reported here are from a single experiment; at least two independent experiments were done for each cell line.

TABLE 2

Doubling times (hours) of breast cancer cell lines

| MDA-MB-231 | −epirubicin | +25 nM epirubicin |
| --- | --- | --- |
| Native | 25 (1.2) | 70 (17.8) |
| 25 nM-Resistant | 40 (4.2) | 43 (3.0) |
| MCF7 | −epirubicin | +30 nM epirubicin |
| Native | 29 (1.9) | 74 (17.2) |
| 30 nM-Resistant | 43 (4.1) | 37 (4.7) |
| SKBR3 | −epirubicin | +15 nM epirubicin |
| Native | 45 (3.2) | 57 (6.6) |
| 15 nM-Resistant | 63 (2.0) | 66 (9.2)* |
| ZR-75-1 | −epirubicin | +10 nM epirubicin |
| Native | 50 (8.1) | 95 (14.2) |
| 10 nM-Resistant | 72 (15.9) | 67 (4.0) |

Data is based on three independent experiments and shows standard deviation in parentheses.
*Indicates data based on two experiments.

TABLE 3

List of 61 common genes consistently differential across all 4 cell lines

| ID | Symbol | Direction | GeoMean | MB231_Log2 Fold Change | MB231_Adjusted p value | MCF7_Log2 Fold change | MCF7_Adjusted p value | SKBR3_Log2 Fold Change | SKBR3_Adjusted p value | ZR_Log2 Fold Change |
|---|---|---|---|---|---|---|---|---|---|---|
| 2650564 | RARRES3 | Up | 3.148596 | 3.653681782 | 3.63673E-06 | 4.447199806 | 4.25784E-07 | 2.768671149 | 9.64747E-05 | 2.184635223 |
| 6180048 | NEDD9 | Up | 2.089221 | 3.741062631 | 7.0176E-07 | 1.58242038 | 0.007340759 | 2.850554148 | 2.09226E-05 | 1.128993412 |
| 5090671 | GDF15 | Up | 2.032681 | 3.636941494 | 7.16273E-09 | 3.804855045 | 6.8255E-09 | 0.768664332 | 0.048864479 | 1.604966347 |
| 3190021 | NTN4 | Up | 1.935478 | 1.241937436 | 0.001851238 | 1.556571883 | 0.000373031 | 1.678774226 | 0.000119633 | 4.324067875 |
| 6760037 | SYTL2 | Up | 1.52817 | 1.1652976 | 0.000296203 | 1.011969203 | 0.001651786 | 2.500169094 | 2.23612E-08 | 1.849749141 |
| 2970019 | HIST1H4H | Up | 1.516285 | 1.80342791 | 3.58277E-07 | 1.090361289 | 0.000225985 | 1.770171737 | 4.13823E-07 | 1.518585301 |
| 4290730 | LGALS3BP | Up | 1.481281 | 0.682098757 | 0.047006282 | 3.964546016 | 1.12565E-09 | 1.447192416 | 0.000270078 | 1.230220759 |
| 2760079 | FOXC1 | Up | 1.455519 | 1.00420363 | 0.1123889 | 1.249522673 | 0.003629325 | 4.20717645 | 9.50527E-10 | 0.850186644 |
| 5670465 | ADM | Up | 1.387493 | 0.487034246 | 0.009289321 | 2.638929722 | 3.75702E-11 | 1.285988414 | 4.96652E-07 | 2.24232699 |
| 1510300 | EIF3 | Up | 1.381065 | 3.98007561 | 2.15212E-14 | 2.091234261 | 1.12565E-09 | 0.431898221 | 0.022036181 | 1.012000235 |
| 290730 | HIST1H2BD | Up | 1.227323 | 1.732788352 | 5.70725E-11 | 0.851313553 | 2.41395E-06 | 1.189402023 | 1.47808E-08 | 1.293217591 |
| 6590594 | HIST1H2AC | Up | 1.225358 | 1.403406756 | 1.31934E-07 | 0.880535196 | 7.12926E-05 | 1.478714456 | 5.67282E-08 | 1.233780479 |
| 6200669 | HIST1H2BD | Up | 1.185078 | 1.617462726 | 3.23951E-08 | 0.733181549 | 0.000702515 | 1.253651241 | 9.9673E-07 | 1.326676757 |
| 3190112 | SERPINB1 | Up | 1.060114 | 1.204186672 | 1.70104E-07 | 1.165070852 | 4.04854E-07 | 1.792280786 | 3.93893E-10 | 0.502294954 |
| 5570279 | HIST1H1C | Up | 1.023357 | 1.027453541 | 0.000193176 | 1.856791331 | 2.39596E-07 | 0.528988612 | 0.032349843 | 1.085769647 |
| 4670592 | MYOF | Up | 0.911692 | 0.777614107 | 8.6546E-05 | 1.094263174 | 2.23886E-06 | 1.477305039 | 2.15583E-08 | 0.549587044 |
| 1230767 | IFITM2 | Up | 0.882348 | 0.438443858 | 0.04703333 | 1.239747977 | 1.64764E-06 | 1.681706166 | 1.94374E-07 | 0.663073931 |
| 3170273 | FER1L3 | Up | 0.877948 | 0.804031756 | 9.7142E-05 | 0.80661503 | 0.000141542 | 1.634891191 | 9.81454E-09 | 0.56033448 |
| 7650433 | TMP1 | Up | 0.793399 | 0.595283591 | 0.019559902 | 0.545339978 | 0.040652461 | 0.96714379 | 0.0006404 | 1.262073349 |
| 2810463 | LOC729009 | Up | 0.785447 | 1.539336581 | 9.8671E-07 | 0.505607019 | 0.035909092 | 0.883796598 | 0.000571234 | 0.553310958 |
| 4450139 | FTHL3 | Up | 0.752148 | 1.565607318 | 7.06118E-09 | 0.350509492 | 0.041522483 | 0.923646946 | 8.82241E-06 | 0.631428946 |
| 6110630 | HIST1H2BK | Up | 0.711506 | 0.861411469 | 1.9905E-06 | 0.663913117 | 7.01773E-05 | 0.494068326 | 0.00096232 | 0.905997373 |
| 460164 | FTHL11 | Up | 0.680375 | 1.356498845 | 1.0086E-06 | 0.466130773 | 0.02928065 | 0.587851408 | 0.005957661 | 0.576499038 |
| 730286 | TXNRD1 | Up | 0.66486 | 0.828723276 | 0.000140939 | 1.032238709 | 1.88443E-05 | 0.47312385 | 0.015299184 | 0.482787056 |
| 4280113 | NFKBIA | Up | 0.603038 | 0.443885758 | 0.018039201 | 0.602469714 | 0.003460198 | 0.664679665 | 0.001174192 | 0.743979415 |
| 1510019 | MGST2 | Up | 0.588832 | 0.690699027 | 0.000233532 | 0.888303429 | 2.37996E-05 | 0.356187337 | 0.035432188 | 0.550092348 |
| 4260019 | NGRN | Up | 0.285379 | 0.284273928 | 0.017492979 | 0.286069278 | 0.023278031 | 0.278236487 | 0.022885132 | 0.293131687 |
| 4920053 | BTG3 | Down | 1.057953 | -0.994500313 | 7.60336E-08 | -2.052756871 | 2.71104E-12 | -0.707227434 | 6.47272E-06 | -0.867687244 |
| 2030148 | WDR54 | Down | 0.937605 | -0.697640144 | 4.99278E-05 | -0.695295447 | 7.93894E-05 | -1.225403064 | 3.1976E-08 | -1.300160246 |
| 7210605 | BTG3 | Down | 0.914882 | -0.782708938 | 0.000186404 | -1.882321708 | 4.30457E-09 | -0.52243878 | 0.006715335 | -0.910188702 |
| 3610735 | F12 | Down | 0.821478 | -0.668310659 | 0.001690483 | -0.731457558 | 0.001186424 | -1.698184733 | 3.15998E-08 | -0.548568688 |
| 3460707 | STMN1 | Down | 0.776332 | -0.881249308 | 2.49829E-06 | -1.06145713 | 3.28522E-07 | -0.990321397 | 5.10112E-07 | -0.392113403 |
| 6770608 | BNIP3 | Down | 0.728782 | -0.355313963 | 0.012030965 | -0.896084604 | 2.45297E-06 | -0.707030937 | 3.06142E-05 | -1.253116563 |
| 5960224 | PTTG3P | Down | 0.638443 | -0.594570853 | 0.000701649 | -0.713277749 | 0.000185456 | -0.622173213 | 0.000517861 | -0.62967301 |
| 1510291 | PTTG1 | Down | 0.608276 | -0.586131618 | 0.000147683 | -0.878266532 | 1.99227E-06 | -0.459314456 | 0.001625214 | -0.578990073 |
| 3460187 | UAP1 | Down | 0.605505 | -0.609999942 | 7.63221E-05 | -0.345489059 | 0.013592559 | -0.530382744 | 0.000344145 | -1.202591574 |
| 6330343 | LOC400013 | Down | 0.6027 | -1.497139045 | 2.514E-10 | -1.197310666 | 1.29734E-08 | -0.255806511 | 0.0476818 | -0.287799173 |

TABLE 3-continued

List of 61 common genes consistently differential across all 4 cell lines

| ID | Symbol | Direction | GeoMean | MB231_Log2 Fold Change | MB231_Adjusted p value | MCF7_Log2 Fold change | MCF7_Adjusted p value | SKBR3_Log2 Fold Change | SKBR3_Adjusted p value | ZR_Log2 Fold Change |
|---|---|---|---|---|---|---|---|---|---|---|
| 4390484 | TACC3 | Down | 0.593789 | −0.626709097 | 0.000129782 | −0.657393468 | 0.00011824 | −0.283671092 | 0.049577036 | −1.063709121 |
| 2000593 | RPL17 | Down | 0.577385 | −0.588811817 | 0.00541746 | −0.501744259 | 0.020892276 | −0.70368187 | 0.001591708 | −0.534634337 |
| 5260538 | C9ORF30 | Down | 0.576402 | −0.369061183 | 0.031841007 | −0.719125251 | 0.000377899 | −0.781155377 | 0.000113485 | −0.532427825 |
| 3870577 | MFSD10 | Down | 0.574913 | −0.393204338 | 0.000955945 | −1.018383073 | 1.6896E-08 | −0.445862974 | 0.000332799 | −0.611895834 |
| 2470333 | TBPL1 | Down | 0.569527 | −0.790059852 | 0.000223837 | −0.516164639 | 0.010887416 | −0.392221311 | 0.041959994 | −0.657777182 |
| 4890093 | BRP44L | Down | 0.552822 | −0.905230881 | 0.00013697 | −0.918490682 | 1.64274E-07 | −0.472373824 | 0.000320624 | −0.422733179 |
| 383092 | RGS10 | Down | 0.551694 | −0.599276133 | 0.001336879 | −0.482359577 | 0.009910653 | −0.633949005 | 0.000933824 | −0.505522085 |
| 5860707 | SAAL1 | Down | 0.543692 | −0.441887147 | 0.001870805 | −0.905719329 | 1.26247E-06 | −0.301083107 | 0.027747176 | −0.725135442 |
| 5130497 | S100A13 | Down | 0.537715 | −0.3731618 | 0.022268267 | −0.532321743 | 0.003150339 | −1.025263414 | 2.1919E-06 | −0.410489866 |
| 2510278 | MAD2L2 | Down | 0.518602 | −0.314700606 | 0.022350536 | −0.720882199 | 3.15681E-05 | −0.3321464 | 0.019159199 | −0.959945984 |
| 4860086 | TMEM118 | Down | 0.510012 | −0.431073739 | 0.00618594 | −0.357621648 | 0.026680875 | −0.32636258 | 0.036611528 | −1.34476073 |
| 5960253 | TRMT5 | Down | 0.496152 | −0.854734207 | 6.53583E-07 | −0.668965367 | 2.47573E-05 | −0.279863322 | 0.028979187 | −0.374305702 |
| 1410309 | LOC200030 | Down | 0.478234 | −0.681355125 | 0.000102772 | −0.79004931 | 3.01351E-05 | −0.312093958 | 0.0424021 | −0.311344924 |
| 5960021 | HS.57079 | Down | 0.471627 | −0.300585974 | 0.014673571 | −0.285037365 | 0.02698542 | −2.070268939 | 8.65337E-13 | −0.278931657 |
| 6620356 | ARPP19 | Down | 0.442397 | −0.321869883 | 0.014853613 | −0.302991326 | 0.028320302 | −0.528950623 | 0.000357123 | −0.742545896 |
| 1580603 | ATP5I | Down | 0.442257 | −0.627441919 | 2.37616E-06 | −0.414234377 | 0.000397532 | −0.296398647 | 0.005183639 | −0.49659544 |
| 6420446 | CMPK1 | Down | 0.441949 | −0.750473772 | 3.8767E-05 | −0.335178786 | 0.034964112 | −0.456565239 | 0.004452136 | −0.332179689 |
| 1510180 | LOC100130178 | Down | 0.439856 | −0.261347038 | 0.012650558 | −0.491648564 | 9.41264E-05 | −0.488091279 | 7.03782E-05 | −0.596857031 |
| 1450674 | LOC730534 | Down | 0.424832 | −0.682052148 | 8.54419E-06 | −0.525804233 | 0.000237981 | −0.283328604 | 0.022515347 | −0.320580401 |
| 4760020 | UROD | Down | 0.409187 | −0.475845157 | 0.000536956 | −0.438340937 | 0.001666825 | −0.40946835 | 0.002206143 | −0.328237685 |
| 4730605 | AURKA | Down | 0.408034 | −0.281668226 | 0.042610896 | −0.969683657 | 1.02228E-06 | −0.291324158 | 0.042601704 | −0.348371683 |
| 650291 | NHP2 | Down | 0.376524 | −0.235508145 | 0.045581381 | −0.930566464 | 2.15841E-07 | −0.276751743 | 0.024576203 | −0.33138139 |
| 1510202 | RWDD1 | Down | 0.362583 | −0.239714468 | 0.045435999 | −0.469491498 | 0.000779742 | −0.509735867 | 0.000256759 | −0.301275026 |
| 622036 | POGK | Down | 0.338358 | −0.226483407 | 0.034515599 | −0.310872883 | 0.00784246 | −0.389835437 | 0.001038556 | −0.47536144 |

TABLE 4

Percent reduction in gene expression compared to non-targeting siRNA control

| | MDA-MB-231 Epi-R | | ZR-75-1 Epi-R | |
|---|---|---|---|---|
| | H2AC expression | H2BK expression | H2AC expression | H2BK expression |
| siH2AC | 24.4 (±3.2) | — | 27.5 (±0.16) | — |
| SiH2BK | — | 12.2 (±2.5) | — | 5.7 (±1.44) |
| siH2BA and siH2BK | 40.7 (±10.9) | 12.2 (±3.7) | 52.8 (±0.99) | 7.9 (±2.25) |

TABLE 5

Drugs targeting epirubicin resistant breast cancer cells

| | | IC,n values (µM) | | | | | | | |
|---|---|---|---|---|---|---|---|---|---|
| Drug status | Drug name | MCF7 Nat | MCF7 EpiR | 231 Nat | 231 EpiR | SKBR3 Nat | SKBR3 EpiR | ZR75 Nat | ZR75 EpiR |
| Phase I | Panobinostat (LBH-589) | 0.01 | 0.01 | 0.02 | 0.01 | 0.02 | 0.07 | 0.01 | 0.02 |
| Phase | Quisinostat (JNJ-26481585) | 0.01 | 0.01 | 0.01 | 0.01 | 0.01 | 0.22 | 0.01 | 0.01 |
| Phase | Givinostat (ITF2357) | 0.10 | 0.08 | 0.26 | 0.16 | 0.22 | 2.74 | 0.17 | 0.18 |
| Phase | Abexinostat (PCI-24781) | 0.11 | 0.09 | 0.27 | 0.12 | 0.21 | 2.25 | 0.14 | 0.16 |
| Phase | Pracinostat (58939) | 0.16 | 0.12 | 0.54 | 0.18 | 0.26 | 0.92 | 0.15 | 0.23 |
| Phase | Belinostat (PX-10 5684) | 0.25 | 0.20 | 0.50 | 0.18 | 0.21 | 0.15 | 0.36 | 0.46 |
| Phase | Mocetinostat (MGCD0103) | 0.32 | 0.41 | 0.85 | 0.43 | 1.00 | 3.69 | 0.35 | 0.43 |
| Preclinical | Apicidin A (051-2040) | 0.07 | 0.11 | 0.23 | 0.11 | 0.17 | 2.21 | 0.21 | 0.25 |
| Preclinical | CAY10 603 (5T-2-92) | 0.61 | 0.38 | 1.27 | 0.82 | 0.44 | 1.03 | 0.98 | 0.75 |
| Preclinical | Oxamflatin (107-0130) | 0.62 | 0.25 | 0.59 | 0.29 | 1.28 | 0.69 | 0.68 | 1.20 |
| Preclinical | Trichostatin A | 1.18 | 0.50 | 0.33 | 0.15 | 1.52 | 1.24 | 1.83 | 2.28 |
| Preclinical | Scriptaid | 1.34 | 0.72 | 3.81 | 1.30 | 1.25 | 0.94 | 1.66 | 1.23 |
| Tool compound | CBHA | 1.18 | 3.58 | 2.39 | 1.75 | 1.45 | 1.03 | 2.94 | 2.25 |
| Discontinued - Phase I | Dacinostat (LAQ824) | 0.02 | 0.01 | 0.04 | 0.02 | 0.02 | 0.06 | 0.02 | 0.02 |

TABLE 6

List of primary antibodies

| Antibody | Vendor | Clone |
|---|---|---|
| anti-EGFR | Santa Cruz Biotech | A-10 |
| anti-PR | Dako | PgR 636 |
| anti-HER2 | Cell Signaling Technology | Polyclonal (#2242) |
| anti-HER3 | Dako | DAK-H3-IC |
| anti-ERα | Novocastra/Leica | ER 6F11 |
| anti-MDR1 | Santa Cruz Biotech | G-1 |
| anti-TOPOIIα | Cell Signaling Technology | D10G9 |
| anti-H2A | Cell Signaling Technology | Polyclonal (#2578) |
| anti-H2B | Cell Signaling Technology | 53H3 |
| anti-actin | Calbiochem | JLA20 |
| anti-GAPDH | Cell Signaling Technology | D16H11 |

TABLE 7

List of histone module genes in the NanoString codeset

HIST1H2BK
HIST1H2BD
NEDD9
SYTL2
NHP2
ARPP19
TXNRD1
CENPF
STMN1
CCT5
APRT
UBEC2C

TABLE 7-continued

List of histone module genes in the NanoString codeset

BAX
HDAC1
E2F1
E2F2
E2F4
CDKN2A

REFERENCE LIST

Bartlett J M, McConkey C C, Munro A F, Desmedt C, Dunn J A, Larsimont D P, O'Malley F P, Cameron D A, Earl H M, Poole C J, Shepherd L E, Cardoso F, Jensen M B, Caldas C, Twelves C J, Rea D W, Ejlertsen B, Di L A and Pritchard K I. (2015). *J Clin Oncol.* 33(15),1680-7

Beck H C, Nielsen E C, Matthiesen R, Jensen L H, Sehested M, Finn P, Grauslund M, Hansen A M and Jensen O N. (2006). *Mol Cell Proteomics,* 5, 1314-1325.

Bonenfant D, Coulot M, Towbin H, Schindler P and van O J. (2006). *Mol Cell Proteomics,* 5, 541-552.

Chazard M, Pellae-Cosset B, Garet F, Soares J A, Lucidi B, Lavail Y and Lenaz L. (1994). *Bull Cancer,* 81, 173-181.

de Jong S, Zijlstra J G, de Vries E G and Mulder N H. (1990). *Cancer Res,* 50, 304-309.

Early Breast Cancer Trialists' Collaborative Group (EBCTCG). (2005). *Lancet,* 365, 1687-1717.

Friesen C, Fulda S and Debatin K M. (1997). *Leukemia,* 11, 1833-1841.

Giaccone G, Gazdar A F, Beck H, Zunino F and Capranico G. (1992). *Cancer Res,* 52, 1666-1674.

Gosland M P, Gillespie M N, Tsuboi C P, Tofiq S, Olson J W, Crooks P A and Aziz S M. (1996). *Cancer Chemother Pharmacol,* 37, 593-600.

Groselj B, Sharma N L, Hamdy F C, Kerr M and Kiltie A E. (2013). *Br J Cancer,* 108, 748-754.

Guo B, Villeneuve D J, Hembruff S L, Kirwan A F, Blais D E, Bonin M and Parissenti A M. (2004). *Breast Cancer Res Treat,* 85, 31-51.

Gyorffy B, Lanczky A, Eklund A C, Denkert C, Budczies J, Li Q and Szallasi Z. (2010). *Breast Cancer Res Treat,* 123, 725-731.

Harris M E, Bohni R, Schneiderman M H, Ramamurthy L, Schumperli D and Marzluff W F. (1991). *Mol Cell Biol,* 11, 2416-2424.

Hembruff S L, Laberge M L, Villeneuve D J, Guo B, Veitch Z, Cecchetto M and Parissenti A M. (2008). *BMC Cancer,* 8, 318.

Kanehisa M, Goto S, Sato Y, Kawashima M, Furumichi M and Tanabe M. (2014). *Nucleic Acids Res,* 42, D199-D205.

Lee J H, Choy M L and Marks P A. (2012). *Adv Cancer Res,* 116, 39-86.

Lowe S W, Ruley H E, Jacks T and Housman D E. (1993). *Cell,* 74, 957-967.

Minotti G, Menna P, Salvatorelli E, Cairo G and Gianni L. (2004). *Pharmacol Rev,* 56, 185-229.

Munro A F, Twelves C, Thomas J S, Cameron D A and Bartlett J M. (2012). *Br J Cancer,* 107, 71-74.

Paridaens R, Biganzoli L, Bruning P, Klijn J G, Gamucci T, Houston S, Coleman R, Schachter J, Van V A, Sylvester R, Awada A, Wildiers J and Piccart M. (2000). *J Clin Oncol,* 18, 724-733.

Parra M A, Kerr D, Fahy D, Pouchnik D J and Wyrick J J. (2006). *Mol Cell Biol,* 26, 3842-3852.

Parra M A and Wyrick J J. (2007). *Mol Cell Biol,* 27, 7641-7648.

Perou C M, Sorlie T, Eisen M B, van de Rijn M, Jeffrey S S, Rees C A, Pollack J R, Ross D T, Johnsen H, Akslen L A, Fluge O, Pergamenschikov A, Williams C, Zhu S X, Lonning P E, Borresen-Dale A L, Brown P O and Botstein D. (2000). *Nature,* 406, 747-752.

Poole C J, Earl H M, Hiller L, Dunn J A, Bathers S, Grieve R J, Spooner D A, Agrawal R K, Fernando I N, Brunt A M, O'Reilly S M, Crawford S M, Rea D W, Simmonds P, Mansi J L, Stanley A, Harvey P, McAdam K, Foster L, Leonard R C and Twelves C J. (2006). 355, 1851-1862.

Pritchard K I, Munro A, O'Malley F P, Tu D, Li X, Levine M N, Shepherd L, Chia S and Bartlett J M. (2012). *Breast Cancer Res Treat,* 131, 541-551.

Regel I, Merkl L, Friedrich T, Burgermeister E, Zimmermann W, Einwachter H, Herrmann K, Langer R, Rocken C, Hofheinz R, Schmid R and Ebert M P. (2012). *Gastroenterology,* 143, 99-109.

Ringel I and Horwitz S B. (1991). *J Natl Cancer Inst,* 83, 288-291.

Schinkel A H, Roelofs E M and Borst P. (1991). *Cancer Res,* 51, 2628-2635.

Sorlie T, Perou C M, Tibshirani R, Aas T, Geisler S, Johnsen H, Hastie T, Eisen M B, van de Rijn M, Jeffrey S S, Thorsen T, Quist H, Matese J C, Brown P O, Botstein D, Lonning P E and Borresen-Dale A L. (2001). *Proc Natl Acad Sci USA,* 98, 10869-10874.

van der Bliek A M, Baas F, Van d, V, Biedler J L, Meyers M B, Ozols R F, Hamilton T C, Joenje H and Borst P. (1988). *Cancer Res,* 48, 5927-5932.

Wagner J M, Hackanson B, Lubbert M and Jung M. (2010). *Clin Epigenetics,* 1, 117-136.

Whitfield M L, Zheng L X, Baldwin A, Ohta T, Hurt M M and Marzluff W F. (2000). *Mol Cell Biol,* 20, 4188-4198.

Wyrick J J and Parra M A. (2009). *Biochim Biophys Acta,* 1789, 37-44.

Breitling R, Armengaud P, Amtmann A and Herzyk P. (2004). *FEBS Lett,* 573, 83-92.

The invention claimed is:

1. A method for determining a likelihood of resistance to anthracycline in a patient with breast cancer comprising:
   a. providing a sample from the patient;
   b. detecting a level of expression in the sample of genes comprising HIST1H2BK, HIST1H2BD, NEDD9, SYTL2, NHP2, ARPP19, TXNRD1, CENPF, STMN1, CCT5, APRT, UBEC2C, BAX, HDAC1, E2F1, E2F2, E2F4, and CDKN2A;
   c. comparing the level of the genes detected in b. to a level of expression of the genes in a control sample; and
   wherein there is a likelihood of anthracycline resistance if there is a higher level of expression of the genes in the patient sample compared to the control sample.

2. The method of claim 1, further comprising treating the patient with adjuvant therapy that does not comprise anthracycline if there is a higher level of expression of the genes in the subject sample compared to the control sample.

3. The method of claim 1, further comprising administering to the patient anthracycline along with a histone deacetylase inhibitor.

4. The method of claim 3, wherein the histone deacetylase inhibitor is panobinostat, quisinostat, givinostat, abexinostat, pracinostat, belinostat mocetinostat, Apicidin A, CAY10603, Oxamflatin, Trichostatin A, Sciptaid, CBHA or Dacinostat.

5. The method of claim 1, wherein the breast cancer is early breast cancer.

6. The method of claim 1, wherein the anthracycline is Daunorubicin Doxorubicin, Epirubicin, Idarubicin, Valrubicin, or Mitoxantrone.

7. The method of claim 6, wherein the anthracycline is Epirubicin.

8. The method of claim 1, wherein the genes, detected for expression levels, consist of HIST1H2BK, HIST1H2BD, NEDD9, SYTL2, NHP2, ARPP19, TXNRD1, CENPF, STMN1, CCT5, APRT, UBEC2C, BAX, HDAC1, E2F1, E2F2, E2F4, and CDKN2A.

9. The method of claim 5, wherein the breast cancer is ER+HER2−, luminal A, ER+HER2+, luminal B, ER−HER2+, HER2−amplified, and ER−/PR−/HER2−, or triple negative.

* * * * *